(12) United States Patent
Gunderson et al.

(10) Patent No.: US 12,048,516 B2
(45) Date of Patent: Jul. 30, 2024

(54) BODY STABILITY MEASUREMENT USING PULSE TRANSIT TIME

(71) Applicant: Medtronic, Inc., Minneapolis, MN (US)

(72) Inventors: Bruce D. Gunderson, Plymouth, MN (US); Eduardo N. Warman, Maple Grove, MN (US); Mirko de Melis, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 284 days.

(21) Appl. No.: 17/086,653

(22) Filed: Nov. 2, 2020

(65) Prior Publication Data

US 2021/0127992 A1     May 6, 2021

Related U.S. Application Data

(60) Provisional application No. 62/930,135, filed on Nov. 4, 2019.

(51) Int. Cl.
*A61B 5/021* (2006.01)
*A61B 5/00* (2006.01)

(52) U.S. Cl.
CPC .......... *A61B 5/02125* (2013.01); *A61B 5/686* (2013.01); *A61B 5/746* (2013.01); *A61B 2562/0219* (2013.01)

(58) Field of Classification Search
None
See application file for complete search history.

(56) References Cited

U.S. PATENT DOCUMENTS

| | | | |
|---|---|---|---|
| 5,788,643 | A | 8/1998 | Feldman |
| 6,336,903 | B1 | 1/2002 | Bardy |
| 6,480,733 | B1 | 11/2002 | Turcott |

(Continued)

FOREIGN PATENT DOCUMENTS

| | | | |
|---|---|---|---|
| CN | 101175530 | A | 5/2008 |
| CN | 103415319 | A | 11/2013 |

(Continued)

OTHER PUBLICATIONS

Gholamhosseini et al., "Smartphone-based blood pressure monitoring for falls risk assessment: techniques and technologies," Human Monitoring, Smart Health and Assisted Living: Techniques and Technologies, May 31, 2017, pp. 203-215.

(Continued)

*Primary Examiner* — Devin B Henson
*Assistant Examiner* — Matthew Eric Ogles
(74) *Attorney, Agent, or Firm* — Shumaker & Sieffert, P.A.

(57) ABSTRACT

An example medical device system and method includes accelerometer circuitry configured to generate at least one signal, a memory, and processing circuitry coupled to the accelerometer circuitry and the memory. The processing circuitry is configured to determine a first plurality of pulse transit times (PTTs), determine, based on the at least one accelerometer signal, a Sit-to-Stand transition, determine, based on the Sit-to-Stand transition occurring, a second plurality of PTTs after the Sit-to-Stand transition, and determine a likelihood that a person, such as a patient, may fall based on the first plurality of PTTs and the second plurality of PTTs.

12 Claims, 11 Drawing Sheets

(56) References Cited

U.S. PATENT DOCUMENTS

| | | |
|---|---|---|
| 7,029,447 B2 | 4/2006 | Rantala |
| 7,460,909 B1 | 12/2008 | Koh et al. |
| 8,062,227 B2 | 11/2011 | Cho et al. |
| 8,323,189 B2 | 12/2012 | Tran et al. |
| 8,346,332 B2 | 1/2013 | Kuhn et al. |
| 8,380,303 B2 | 2/2013 | Rosenberg et al. |
| 8,491,485 B2 | 7/2013 | Czygan et al. |
| 8,515,537 B2 | 8/2013 | Cinbis et al. |
| 8,708,924 B2 | 4/2014 | Wariar et al. |
| 8,821,404 B2 | 9/2014 | Thakur et al. |
| 8,886,296 B2 | 11/2014 | Patel |
| 9,174,054 B1 | 11/2015 | Nabutovsky et al. |
| 9,662,073 B2 | 5/2017 | Zhang et al. |
| 9,669,218 B2 | 6/2017 | Libbus et al. |
| 9,826,939 B2 | 11/2017 | Averina et al. |
| 10,172,568 B2 | 1/2019 | Sharma et al. |
| 10,252,068 B2 | 4/2019 | Gunderson et al. |
| 10,610,132 B2 | 4/2020 | Gunderson et al. |
| 10,850,113 B2 | 12/2020 | Cao et al. |
| 11,154,249 B2 | 10/2021 | Kuhn et al. |
| 2007/0115277 A1* | 5/2007 | Wang .............. A61B 5/1116 345/419 |
| 2007/0260285 A1 | 11/2007 | Libbus et al. |
| 2008/0228090 A1 | 9/2008 | Wariar et al. |
| 2009/0062667 A1 | 3/2009 | Fayram et al. |
| 2009/0326350 A1 | 12/2009 | Kracker |
| 2010/0010338 A1* | 1/2010 | van Dam .............. A61B 5/0031 607/60 |
| 2010/0041970 A1 | 2/2010 | Hedberg et al. |
| 2010/0113944 A1* | 5/2010 | Min .............. A61B 5/6846 600/490 |
| 2010/0274219 A1* | 10/2010 | Wenzel .............. A61B 5/388 607/3 |
| 2011/0009754 A1 | 1/2011 | Wenzel et al. |
| 2011/0098771 A1 | 4/2011 | Thakur et al. |
| 2011/0105932 A1* | 5/2011 | Bauer .............. A61B 5/4818 600/528 |
| 2011/0106201 A1 | 5/2011 | Bhunia |
| 2011/0172504 A1 | 7/2011 | Wegerich |
| 2011/0230771 A1 | 9/2011 | Koh et al. |
| 2012/0109243 A1 | 5/2012 | Hettrick et al. |
| 2012/0133602 A1* | 5/2012 | Kamamoto .............. G16H 80/00 345/173 |
| 2012/0172680 A1 | 7/2012 | Gelfand et al. |
| 2013/0116578 A1 | 5/2013 | An et al. |
| 2013/0123617 A1 | 5/2013 | Sola i Caros et al. |
| 2013/0179139 A1* | 7/2013 | Lee .............. A61B 5/165 703/11 |
| 2013/0184545 A1 | 7/2013 | Blomqvist et al. |
| 2013/0237948 A1 | 9/2013 | Donders et al. |
| 2014/0195168 A1 | 7/2014 | Shaihk |
| 2014/0221849 A1 | 8/2014 | Farringdon et al. |
| 2014/0276928 A1 | 9/2014 | Vanderpool et al. |
| 2014/0330172 A1 | 11/2014 | Jovanov et al. |
| 2014/0343371 A1* | 11/2014 | Sowers, II .............. A61B 5/1455 600/323 |
| 2016/0081571 A1* | 3/2016 | Bauer .............. A61B 5/282 600/384 |
| 2016/0095555 A1 | 4/2016 | Stainer et al. |
| 2016/0310031 A1* | 10/2016 | Sarkar .............. A61B 5/287 |
| 2016/0367194 A1* | 12/2016 | Murphy .............. H04N 5/2256 |
| 2017/0100056 A1* | 4/2017 | Zhu .............. H02J 50/10 |
| 2017/0156604 A1 | 6/2017 | Zhang et al. |
| 2017/0209053 A1 | 7/2017 | Pantelopoulos et al. |
| 2017/0231568 A1 | 8/2017 | An et al. |
| 2017/0238812 A1 | 8/2017 | Atlas |
| 2017/0265782 A1 | 9/2017 | Vollmer |
| 2017/0281095 A1 | 10/2017 | An et al. |
| 2017/0347969 A1 | 12/2017 | Thakur et al. |
| 2018/0035898 A1* | 2/2018 | Gunderson .............. A61B 5/287 |
| 2018/0035920 A1 | 2/2018 | Gunderson et al. |
| 2018/0035924 A1 | 2/2018 | Gunderson et al. |
| 2018/0035956 A1 | 2/2018 | Gunderson et al. |
| 2018/0055386 A1* | 3/2018 | Zielinski .............. A61B 5/02108 |
| 2018/0060520 A1* | 3/2018 | Degen .............. G16H 80/00 |
| 2018/0070876 A1 | 3/2018 | Brockway et al. |
| 2018/0177486 A1 | 6/2018 | Gifford, III et al. |
| 2019/0133457 A1 | 5/2019 | Sun et al. |
| 2019/0336076 A1 | 11/2019 | Kuhn et al. |
| 2019/0336077 A1* | 11/2019 | Kuhn .............. A61B 5/14546 |
| 2019/0343415 A1 | 11/2019 | Saha et al. |
| 2020/0187866 A1 | 6/2020 | Antunes et al. |
| 2020/0323452 A1 | 10/2020 | Mahajan et al. |
| 2020/0345309 A1 | 11/2020 | Cheng et al. |
| 2020/0352466 A1 | 11/2020 | Chakravarthy et al. |
| 2020/0352521 A1 | 11/2020 | Chakravarthy et al. |
| 2021/0127992 A1 | 5/2021 | Gunderson et al. |

FOREIGN PATENT DOCUMENTS

| | | | |
|---|---|---|---|
| CN | 104349815 A | 2/2015 | |
| CN | 106659403 A | 5/2017 | |
| EP | 2217140 B1 * | 2/2012 | ......... A61B 5/02125 |
| WO | 2010014066 A | 2/2010 | |
| WO | WO-2016061381 A1 * | 4/2016 | ........... A61B 5/0002 |

OTHER PUBLICATIONS

International Search Report and Written Opinion of International Application No. PCT/US2020/058624, mailed Feb. 8, 2021, 12 pp.

Abay et al., "Reflectance Photoplethysmography as Noninvasive Monitoring of Tissue Blood Perfusion," IEEE Transactions on Biomedical Engineering, vol. 62, No. 9, Sep. 2015, pp. 2187-2195.

Bennett et al., "Development of Implantable Devices for Continuous Ambulatory Monitoring of Central Hemodynamic Values in Heart Failure Patients," Pace, vol. 28, Jun. 2005, pp. 573-584.

Bernard, M.L., "Pacing Without Wires: Leadless Cardiac Pacing," The Ochsner Journal, vol. 16, No. 3, Oct. 2016, 5 pp.

Charach et al., "Internal Thoracic Impedance—A Useful Method for Expedient Detection and Convenient Monitoring of Pleural Effusion," PLOS ONE, published Apr. 28, 2015, 14 pp.

Cowie et al., "Development and validation of an integrated diagnostic algorithm derived from parameters monitored in implantable devices for identifying patients at risk for heart failure hospitalization in an ambulatory setting," European Heart Journal; 43, published online Mar. 19, 2013, pp. 2472-2480.

Edlow et al., "The effects o healthy aging on cerebral hemodynamic responses to posture change," Physiological Measurement, vol. 31, No. 4, Feb. 2010, 19 pp.

Fiala et al., "Implantable Reflectance Pulse Transit Time Blood Pressure Sensor with Oximetry Capability," Proceedings SPIE 7513, 2009 International Conference on Optical Instruments and Technology, vol. 7715, Apr. 28, 2010, 6 pages.

Fontaine et al., "Reflectance-Based Pulse Oximeter for the Chest and Wrist," A Major Qualifying Project Report. Worchester Polytechnic Institute, accessed on Nov. 7, 2017, 96 pp.

Forrester et al., "Correlative Classification of Clinical and Hemodynamic Function after Acute Myocardial Infarction," The American Journal of Cardiology, vol. 39, Issue 2, Feb. 1977, pp. 137-145.

Hogan et al., "Quantitative tissue hemoglobin oxygen saturation measurement in decompensated heart failure," J. Cardiothoracic-Renal Research, May 2006, 1, 153-157.

Hogan et al., "The Utility of Microvascular Perfusion Assessment in Heart Failure: A Pilot Study," J. Cardiac Failure, vol. 11, No. 9, Jul. 2005, pp. 713-719.

Myers et al., "Tissue hemoglobin index: a non-invasive optical measure of total tissue hemoglobin," Critical Care, vol. 13, Suppl. 5, Nov. 30, 2009, 13 pp.

Nohria, MD, et al. "Clinical Assessment Identifies Hemodynamic Profiles that Predict Outcomes in Patients Admitted with Heart Failures," J. Am. Col Cardiology, vol. 41, No. 10, May 21, 2003, 1797-1804.

Podbregar et al., "Skeletal muscle oxygen saturation does not estimate mixed venous oxygen saturation in patients with severe left heart failure and additional severe sepsis or septic shock," Critical Care, Jan. 2007, 11: R6.

(56) References Cited

OTHER PUBLICATIONS

Ponikowski et al. "2016 ESC Guidelines for the diagnosis and treatment of acute and chronic heart failure," European Heart Journal, May 2016, 37, 2129-2200.

Sarkar et al., "A Dynamic Risk Score to Identify Increased Risk for Heart Failure Decompensation," IEEE Transactions on Biomedical Engineering, vol. 60, No. 1, Jan. 2013, pp. 147-150.

Study: "Integrated Diagnostics Driven Diuretic and Chronic Medication Management for Heart Failure." Sponsor: Medtronic Cardiac Rhythm and Heart Failure. https://clinicaltrials.gov/ct2/show/NCT02698241, last updated Apr. 2, 2018, 6 pp.

Virani et al. "Integrated Diagnostics for Heart Failure: The Triage-HF Study," Canadian Journal of Cardiology, Oct. 2016, vol. 32, Issue 10, Supplement 1, pp. S148-S149.

Yancy, MD et al. "2013 ACCF/AHA Guideline for the Management of Heart Failure," Circulation, May 2013, 88 pp. e240-e327.

Yancy, MD et al. "2016 ACC/AHA/HFSA Focused Update on New Pharmacological Therapy for Heart Failure: An Update of the 2013 ACCF/AHA Guideline for the Management of Heart Failure," Journal of Cardiac Failure, vol. 22, No. 9, Sep. 2016, pp. 659-669.

"Causes of Hypoperfusion state," Right Diagnosis, last updated Aug. 13, 2015, accessed from http://www.rightdiagnosis.com/symptoms/hypoperfusion_state/causes.htm, 2 pp.

"VCSEL-ULM763-SingleMODE_TO5_v13," Philips, accessed on Nov. 7, 2017, accessed from http://www.photonics.philips.com/pdf/VCSEL-ULM763-SingleMode_TO5.pdf, 2 pp.

(PCT/US2019/030166) PCT Notification of Transmittal of the International Search Report and the Written Opinion of the International Searching Authority, Mailed Jul. 24, 2019, 14 pages.

International Search Report and Written Opinion of International Application No. PCT/US2019/030202, mailed Jul. 29, 2019, 10 pp.

Auricchio et al., "Reducing Ventricular Pacing Frequency in Patients with Atrioventricular Block", Advances in Arrhythmia and Electrophysiology, vol. 9, No. 9, American Heart Association, Sep. 16, 2016, p. 10.

Fiala et al., "Implantable reflectance pulse transit time blood pressure sensor with oximetry capability", Proceedings SPIE 7513, 2009 International Conference on Optical Instruments and Technology, vol. 7715, Apr. 2010, p. 77152Q.

\* cited by examiner

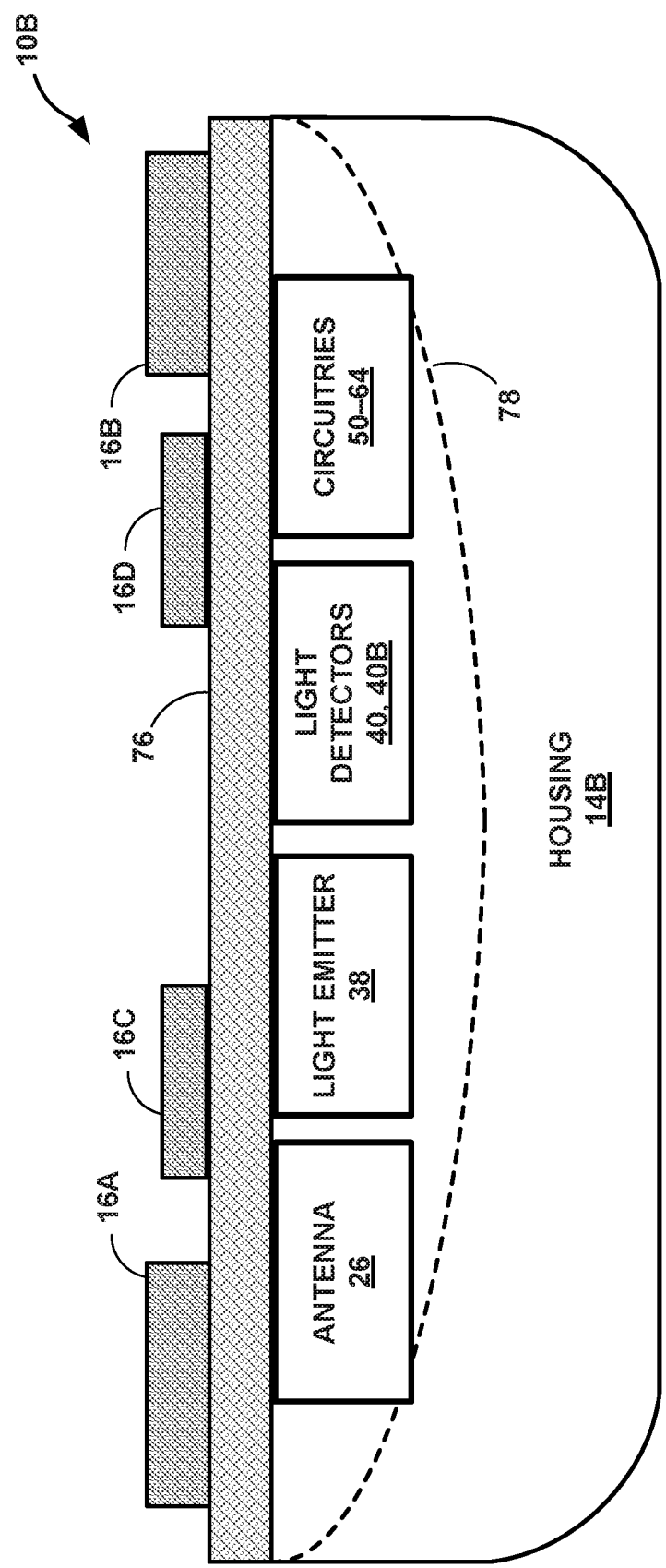

BODY STABILITY MEASUREMENT USING PULSE TRANSIT TIME

This application claims priority to U.S. Provisional Application No. 62/930,135, filed Nov. 4, 2019, the entire content of which is incorporated by reference herein.

TECHNICAL FIELD

The disclosure relates generally to systems for monitoring cardiovascular health, and more particularly to systems configured to monitor body stability and predict the likelihood that a person, such as a patient, may fall based on measured cardiovascular metrics.

BACKGROUND

Implantable medical devices (IMDs) including implantable pacemakers and implantable cardioverter-defibrillators (ICDs) and insertable cardiac monitors without therapies (e.g. Medtronic LINQ™), and external, e.g., wearable medical devices, record cardiac electrogram (EGM) signals for sensing cardiac events, e.g., P-waves and R-waves. Such devices detect episodes of bradycardia, tachycardia and/or fibrillation from the sensed cardiac events, and some devices respond to the episodes as needed with pacing therapy or high-voltage anti-tachyarrhythmia shocks, e.g., cardioversion or defibrillation shocks. These and other medical devices may include, or be part of a system that includes, sensors that generate other physiological-based signals, such as signals that vary based on patient movement or activity, pulse transit time (PTT), cardiovascular pressure, blood oxygen saturation, edema, or thoracic impedance.

PTT may be used to determine a measurement of pulse wave velocity (PWV). PTT indicates the time taken by a pulse wave (e.g., of an ECG signal) to travel over an estimable distance within the patient. In such examples, the estimable distance traveled by the pulse wave may be divided by a determined PTT value to arrive at a PWV value.

SUMMARY

In general, this disclosure is directed to techniques for determining an increase in the likelihood a patient may fall based on a measured PTT. More particularly, this disclosure contemplates a medical system and method that monitors the patient for a Sit-to-Stand transition (e.g., the patient transitioning from a sitting position to a standing position) and measures the patient's PTT prior to and after the Sit-to-Stand transition. People may experience a change in blood pressure when transitioning from a sitting position to a standing position. This change in blood pressure may cause a person to feel light-headed or presyncope. PTT may be a surrogate for blood pressure. By measuring PTT prior to and after a Sit-to-Stand transition, the system and techniques of this disclosure may determine the likelihood that a patient may fall and facilitate changes in treatment of the patient. The PWV value may be used instead of or in addition to the PTT value in assessing the body stability of a patient including the likelihood of the patient falling.

A comparison of current values based on PTT to corresponding baseline values may be used to determine a status of the patient's likelihood of falling. In techniques described herein, one or more IMDs or external devices may determine a PTT and transmit an indication of the patient's body stability or the likelihood of the patient falling to a remote computer or other device external to the patient. The remote computer or other device then may transmit instructions for a medical intervention (e.g., instructions for changes to a drug regimen or physical therapy), to a user device used by the patient or a caregiver. In addition to or as an alternative to transmitting instructions, the remote computer may control the one or more IMDs to deliver a treatment, such as stimulating the heart or a nerve or delivering a drug through a drug pump. In this manner, a patient's treatment may be modified as needed to mitigate the risk of the patient falling.

In some examples, a system is disclosed including accelerometer circuitry configured to generate at least one signal; a memory; and processing circuitry coupled to the accelerometer circuitry and the memory, the processing circuitry being configured to: determine a first plurality of pulse transit times of a patient prior to a Sit-to-Stand transition of the patient; determine, based on the at least one accelerometer signal, whether the Sit-to-Stand transition of the patient occurs; determine, based on the Sit-to-Stand transition occurring, a second plurality of pulse transit times after the Sit-to-Stand transition of the patient; and determine a likelihood the patient will fall based on the first plurality of pulse transit times and the second plurality of pulse transit times.

In other examples, a method is disclosed including determining, by processing circuitry, a first plurality of pulse transit times prior to a Sit-to-Stand transition of a patient; determining, by processing circuitry and based on at least one accelerometer signal, whether the Sit-to-Stand transition of the patient occurs; determining, by processing circuitry and based on the Sit-to-Stand transition occurring, a second plurality of pulse transit times after the Sit-to-Stand transition of the patient; and determining a likelihood the patient will fall based on the first plurality of pulse transit times and the second plurality of pulse transit times.

In other examples, a non-transitory computer-readable storage medium is disclosed comprising instructions, that when executed by processing circuitry of a device, cause the device to: determine a first plurality of pulse transit times prior to a Sit-to-Stand transition of a patient; determine whether the Sit-to-Stand transition of the patient occurs based on at least one accelerometer signal; determine a second plurality of pulse transit times after the Sit-to-Stand transition of the patient; and determine a likelihood the patient will fall based upon the first plurality of pulse transit times and the second plurality of pulse transit times.

This summary is intended to provide an overview of the subject matter described in this disclosure. This summary is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF DRAWINGS

FIGS. 4A and 4B are block diagrams illustrating other example leadless implantable medical devices substantially similar to the implantable medical device of FIG. 1.

DETAILED DESCRIPTION

A medical device system according to certain features or aspects of this disclosure includes accelerometer circuitry configured to generate a number of signals including a sagittal (frontal) axis signal, as well as processing circuitry configured to detect a Sit-to-Stand transition and calculate a plurality of PTTs prior to and after the Sit-to-Stand transition. The system may determine differences between the plurality of PTTs taken after the Sit-to-Stand transition and those taken prior to the Sit-to-Stand transition and monitor those differences over time to determine the likelihood of the patient falling. Such an implementation may, among other things, provide an objective measure of change (or not) in well-being to help guide therapies, because a PTT metric surrounding a Sit-To-Stand transition may help determine whether health is improving, declining, or stable. Although not so limited, an appreciation of the various aspects of the present disclosure may be gained from the following discussion in connection with the drawings. While this disclosure may provide examples, including identifying medical devices that may be configured to implement the techniques described herein, these identifications are not meant to be limiting. Any devices having an accelerometer and/or configured to measure a PTT may be used to implement the techniques of this disclosure.

Figure 1:
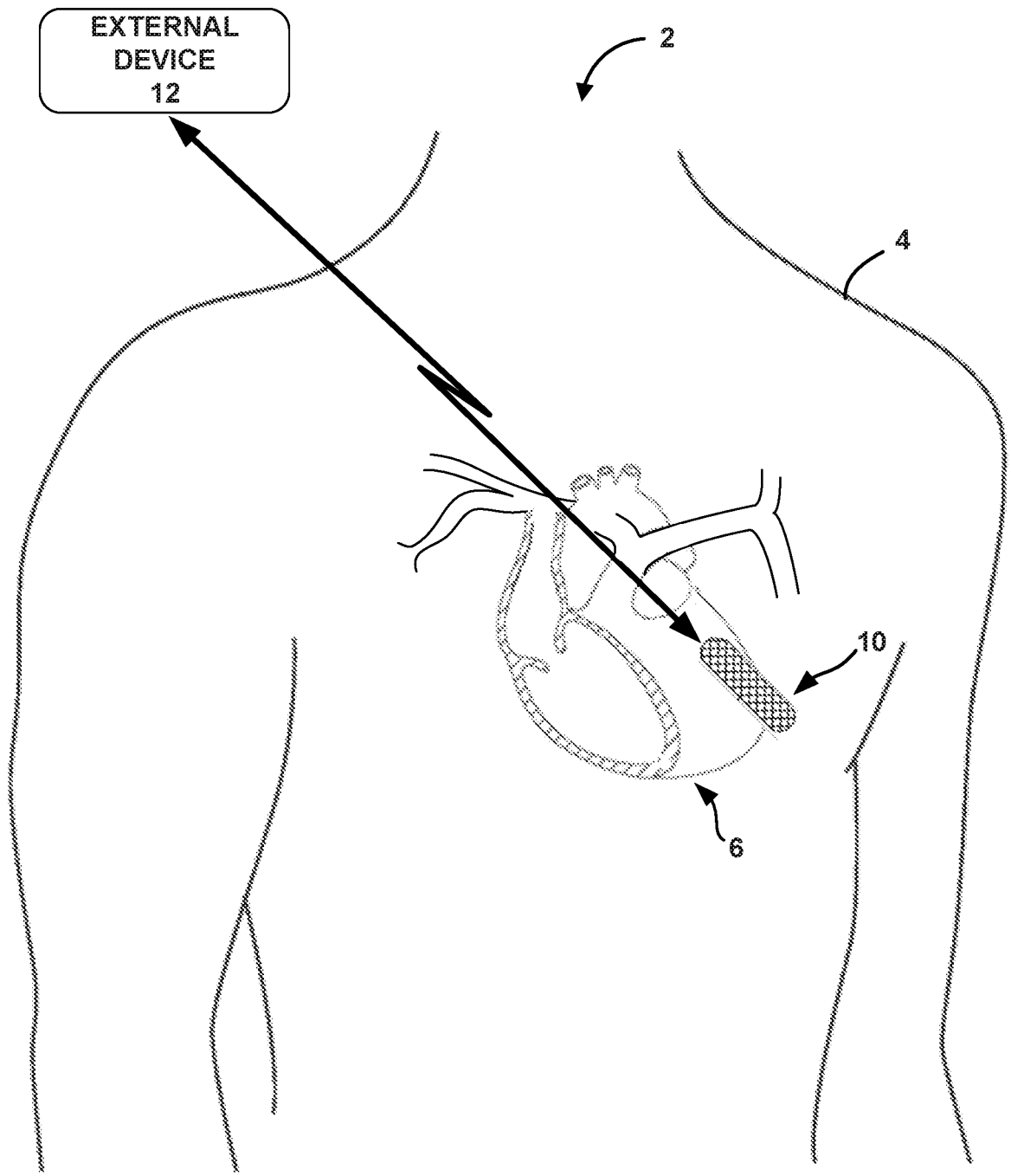
FIG. 1 is a conceptual drawing illustrating an example of a medical device system including a leadless implantable medical device and an external device in conjunction with a patient.

FIG. 1 illustrates the environment of an example medical device system 2 in conjunction with a patient 4 and a heart 6, in accordance with an apparatus and method of certain examples described herein. The example techniques may be used with a leadless subcutaneously-implantable medical device (IMD) 10, which may be in wireless communication with external device 12. In some examples, IMD 10 may be implanted outside of a thoracic cavity of patient 4 (e.g., subcutaneously in the pectoral location illustrated in FIG. 1). IMD 10 may be positioned near the sternum near or just below the level of heart 6, e.g., at least partially within the cardiac silhouette. In some examples, IMD 10 may take the form of a Reveal LINQ™ Insertable Cardiac Monitor (ICM), available from Medtronic plc, of Dublin, Ireland. External device 12 may be a computing device configured for use in settings such as a home, clinic, or hospital, and may further be configured to communicate with IMD 10 via wireless telemetry. For example, external device 12 may be coupled to a remote patient monitoring system, such as Carelink®, available from Medtronic plc, of Dublin, Ireland. External device 12 may, in some examples, comprise a programmer, an external monitor, or a consumer device such as a smart phone or tablet.

IMD 10 may include a plurality of electrodes and one or more optical sensors, which collectively detect signals that enable processing circuitry, e.g., of the IMD 10, to determine values of PTT prior to and after a Sit-to-Stand transition for patient 4, and determine the likelihood that patient 4 may fall based on such values. In some examples, processing circuitry of IMD 10 may determine a Sit-to-Stand transition has occurred based on an accelerometer signal. In some examples, processing circuitry of IMD 10 also may use an ECG signal detected by the plurality of electrodes to determine PTT values of patient 4 prior to and after the Sit-to-Stand transition. In other examples, processing circuitry of IMD 10 may use signals detected by one or more optical sensors positioned on a surface of IMD 10 to determine PTT values in conjunction with the ECG signal prior to and after the Sit-to-Stand transition.

Although not necessarily illustrated in the example of FIG. 1, a medical device system configured to implement the techniques of this disclosure may include one or more implanted or external medical devices in addition to or instead of IMD 10. For example, a medical device system may include a pressure sensing IMD, vascular ICD, extravascular ICD, cardiac pacemaker or other external device. One or more of such devices may generate accelerometer signals, and include processing circuitry configured to perform, in whole or in part, the techniques described herein for determining patient body stability based on accelerometer-generated data. The implanted devices may communicate with each other and/or an external device 12, and one of the implanted or external devices may ultimately calculate PTTs just prior to and after a Sit-To-Stand transition from at least one of a sagittal axis signal, a vertical axis signal and a transverse axis signal.

Accelerometer signals coincident with a sagittal axis of a patient may be leveraged for determining a Sit-To-Stand transition, for example. This is because 3D accelerometers in the IMD 10, which is implanted in the chest, for example, are relatively stationary over the lifetime of the implant. The stationary chest location presents an opportunity to monitor changes in the upper body that occur during various activities. As a patient gets in and out of a chair for example the upper body has a reproducible motion (similar to a "bowing" motion) that may be identified with signals produced by the accelerometers.

After determining PTT values of patient 4 prior to and after the Sit-to-Stand transition, processing circuitry, e.g., of IMD 10, may calculate a first metric based on the first plurality of PTTs (e.g., the PTTs prior to the Sit-to-Stand transition), for example, a mean, median or mode of the first plurality of PTTs. Processing circuitry may also calculate second metrics based on the second plurality of PTTs (e.g., the PTTs after the Sit-to-Stand transition).

In some examples, processing circuitry may also calculate difference metrics between the first metric and the second metrics based on PTT values prior to and after the Sit-to-Stand transition and compare the difference metrics to corresponding baseline values of difference metrics, e.g., stored in a memory of IMD 10, to determine differences therebetween. If the differences between one or more of the PTT difference metrics and corresponding baseline values of difference metrics satisfies a threshold, then the processing circuitry may determine that patient 4 is more likely to fall relative to a time when the baseline values were established.

In addition to or alternatively, processing circuitry, e.g. of IMD 10, may calculate a slope of PTTs after the Sit-to-Stand transition. Processing circuitry, e.g. of IMD 10 may compare the slope of the PTTs after the Sit-to-Stand transition to corresponding baseline value(s) of slope of the PTTs after the Sit-to-Stand transition, e.g., stored in a memory of IMD 10, to determine differences therebetween. If the differences between the slope of the PTTs after the Sit-to-Stand transition and a corresponding baseline satisfies a threshold, then the processing circuitry may determine that patient 4 is more likely to fall relative to a time when the baseline value was established.

Regardless of whether any such differences satisfy a threshold, IMD 10 then may wirelessly transmit data associated with the difference metrics, the slope of the PTTs after the Sit-to-Stand transition and/or PTT values to external device 12. IMD 10 may transmit the data associated with the PTT values to external device 12 at predetermined intervals, such as daily, weekly, or at any other desired period or may transmit the data associated with the difference metrics, the slope of the PTTs after the Sit-to-Stand transition and/or PTT values upon a user request on external device 12.

In some examples, IMD 10 may be configured to undertake a learning phase after implantation into patient 4, in which IMD 10 determines the baseline values of the difference metrics and/or the slope of the PTTs after a Sit-to-Stand transition for patient 4 based on values collected by IMD 10 over a period of time, and stores the baseline values in a memory of IMD 10. For example, IMD 10 may measure PTT prior to and after each Sit-to-Stand for a period of time (e.g., a week or more) to determine baseline values during a period when the physiological condition of patient 4 is stable.

In other examples, instead of determining baseline values, a clinician may select baseline values for patient 4. Lists or tables of such baseline values may be presented by an app on the clinician tablet or other smart device, or may be available from a centralized database. Once the clinician has selected appropriate baseline values for patient 4, the clinician may use the app to store the values in IMD 10.

Values for baselines and thresholds associated with patient 4 may be updated periodically. For example, IMD 10 may undertake a new learning phase daily, weekly, monthly, quarterly, yearly, or at an expiration of any other appropriate period. The new learning phase may produce new values associated with one or more of the baseline values and thresholds of patient 4. In other examples, a clinician may program IMD 10 to update such values as needed, such as following a falling event experienced by patient 4.

In some examples, IMD 10 may determine baseline values based on median, mean or mode PTT values collected during the training period. In other examples, IMD 10 may reject outlier values collected during the training period prior to determining the baseline values. In some examples, a baseline value may be indicative of a value of a difference between a PTT prior to a Sit-to-Stand transition and a PTT after the Sit-to-Stand transition. In addition to determining baseline values for patient 4, IMD 10 or a clinician also may determine threshold values for patient 4 and store the threshold values in a memory of IMD 10.

IMD 10 may determine threshold values for each of a number of different baseline values, such as during the training period of IMD 10. In some examples, IMD 10 may automatically associate a particular threshold value with a particular baseline value for patient 4. In some examples, the thresholds may be determined using Statistical Process Control (SPC) of the baseline for comparison to the current value (e.g., a corresponding current difference metric). In such examples, the thresholds may be useful in detecting an acute change in the falling risk of patient 4. In other examples, Change Point Analysis (CPA) may be applied to determine if there has been a significant change in the slope of PTT after a Sit-to-Stand transition with a time series of slope values (e.g., different slopes measured over time) from the baseline slope value. A significant change in the slope of PTT after a Sit-to-Stand transition with a time series of slope values from the baseline slope value may be indicative of a chronic change in the falling risk of patient 4. The SPC and/or the CPA may be performed by IMD 10, external device 12 or external device 94 (of FIG. 6), for example. In other examples, a clinician may choose to program IMD 10 to apply relatively higher or lower thresholds than those selected by processing circuitry of IMD 10 based on other considerations known to the clinician.

Regardless of whether the threshold values are determined by processing circuitry of IMD 10 during a training period or by a clinician, such threshold values may be updated at one or more times after implantation of IMD 10. For example, threshold values may be updated after patient 4 experiences a falling event. Or, the threshold values may be updated at the expiration of a time period (e.g., weekly, monthly, or yearly following implantation of IMD 10). Such updates to the threshold values may be performed automatically by processing circuitry of IMD 10, or manually by a clinician. In any such examples, the updated threshold values may be determined based on trends in PTT during the preceding time period. In this manner, the threshold values used in the techniques described herein may be modified as needed to account for changes in patient 4's health.

External device 12 may be used to program commands or operating parameters into IMD 10 for controlling its functioning (e.g., when configured as a programmer for IMD 10). In some examples, external device 12 may be used to interrogate IMD 10 to retrieve data, including device operational data as well as physiological data accumulated in IMD memory. Such interrogation may occur automatically according to a schedule, or may occur in response to a remote or local user command. Programmers, external monitors, and consumer devices are examples of external devices 12 that may be used to interrogate IMD 10. Examples of communication techniques used by IMD 10 and external device 12 include radiofrequency (RF) telemetry, which may be an RF link established via Bluetooth®, a wireless local area network, or medical implant communication service (MICS). In some examples, external device 12 may include a user interface configured to allow a clinician to remotely interact with IMD 10.

Medical system 2 is an example of a medical device system configured to determine a patient's risk of falling by monitoring PTT prior to and after a Sit-to-Stand transition. The techniques described herein may be performed by processing circuitry of a device of medical system 2, such as processing circuitry of IMD 10. Additionally, or alternatively, the techniques described herein may be performed, in whole or in part, by processing circuitry of external device 12, and/or by processing circuitry of one or more other implanted or external devices or servers not shown. Examples of the one or more other implanted or external devices may include a transvenous, subcutaneous, or extravascular pacemaker or implantable cardioverter-defibrillator (ICD), a blood analyzer, an external monitor, or a drug pump. The communication circuitry of each of the devices of system 2 allows the devices to communicate with one another. In addition, although the optical sensors and electrodes are described herein as being positioned on a housing of IMD 10, in other examples, such optical sensors and/or electrodes may be positioned on a housing of another device implanted in or external to patient 4, such as a transvenous, subcutaneous, or extravascular pacemaker or ICD, or coupled to such a device by one or more leads. For example, electrodes or one or more optical sensors for detecting signals associated with PTT may be positioned on one or more external monitoring devices (e.g., a wearable monitor). In such examples, one or more of the pacemaker/ICD and the one or more external monitoring devices may include processing circuitry configured to receive signals from the electrodes or optical sensors on the respective devices and/or communication circuitry configured to transmit the signals from the electrodes or optical sensors to another device (e.g., external device 12) or server.

Figure 2:
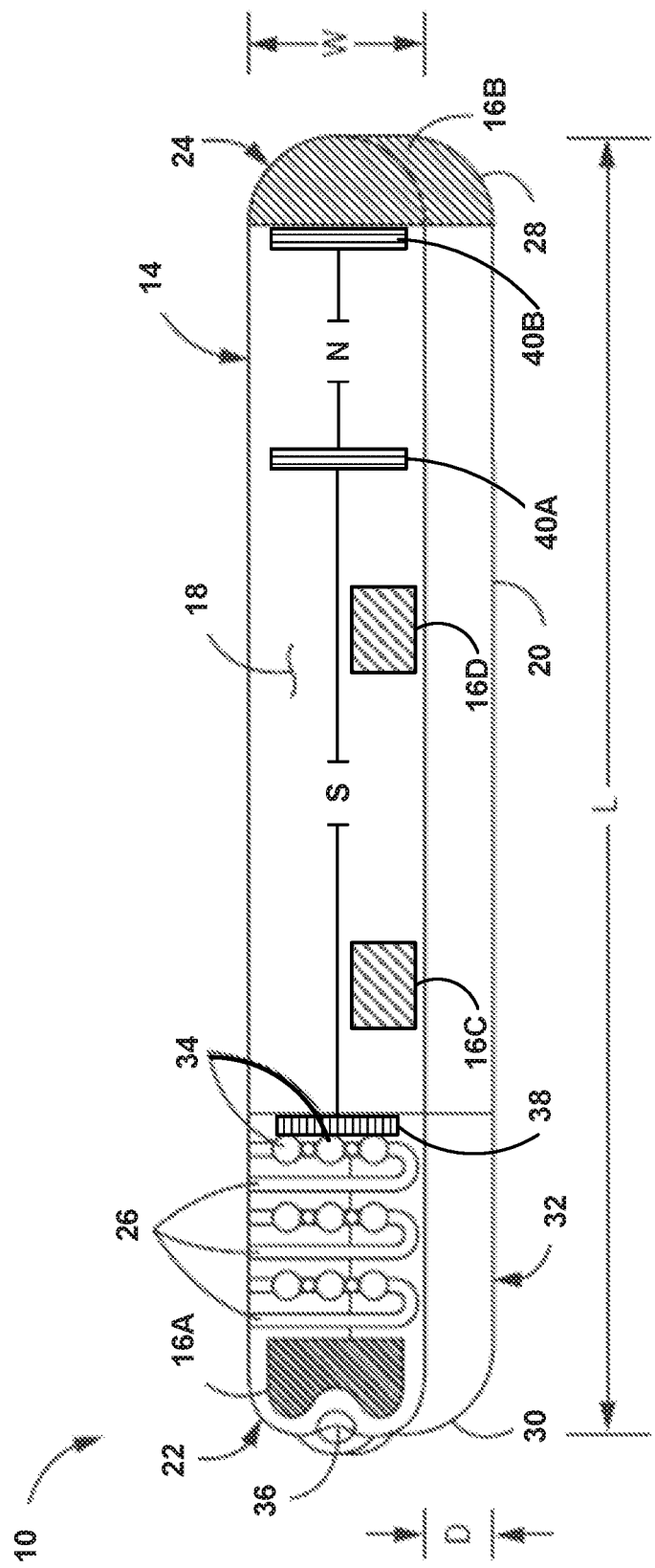
FIG. 2 is a conceptual drawing illustrating an example configuration of the leadless implantable medical device of the medical device system of FIG. 1.
Figure 3:
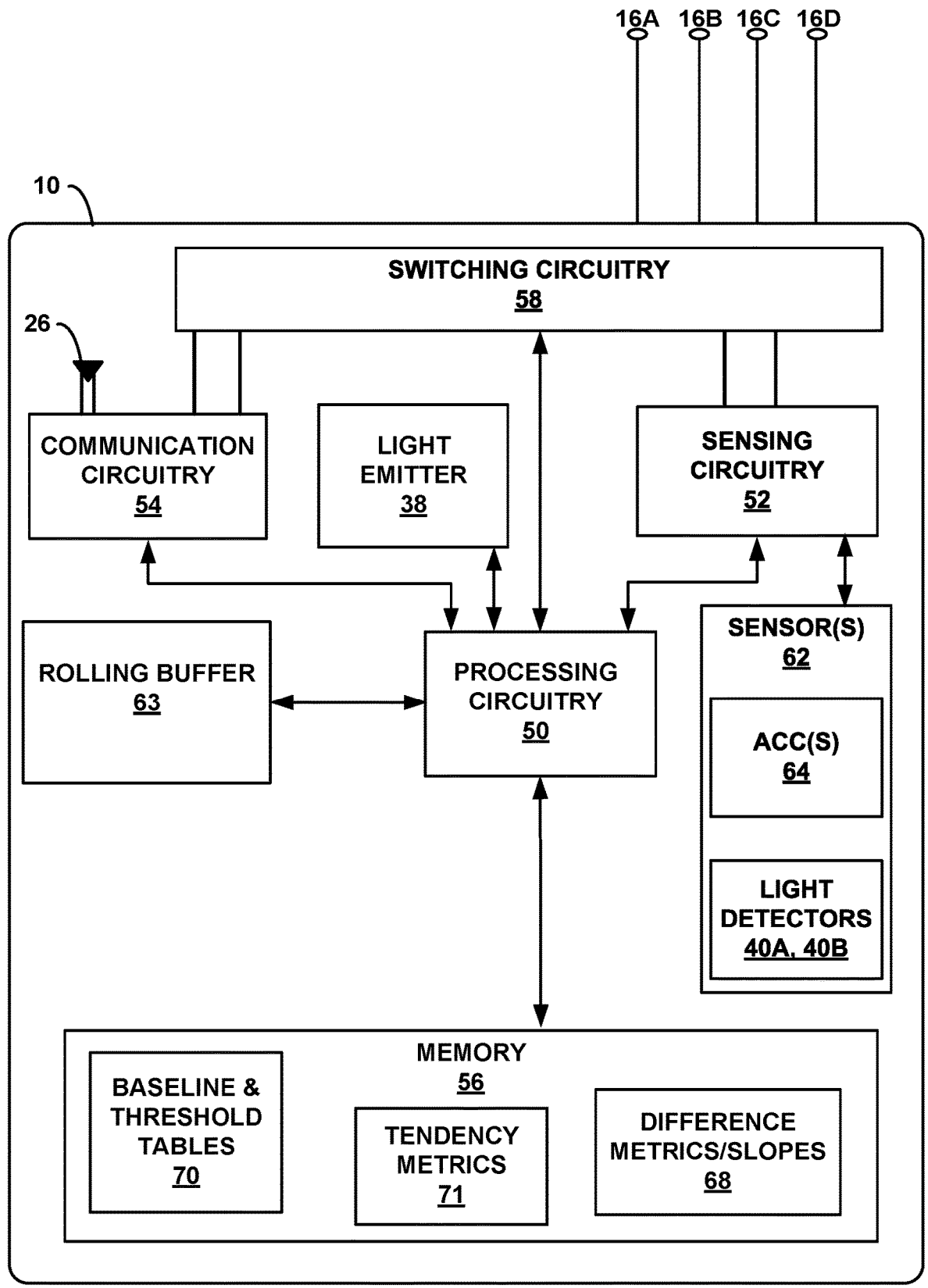
FIG. 3 is a functional block diagram illustrating another perspective of the example configuration of the leadless implantable medical device of FIG. 1.
Figure 4A:
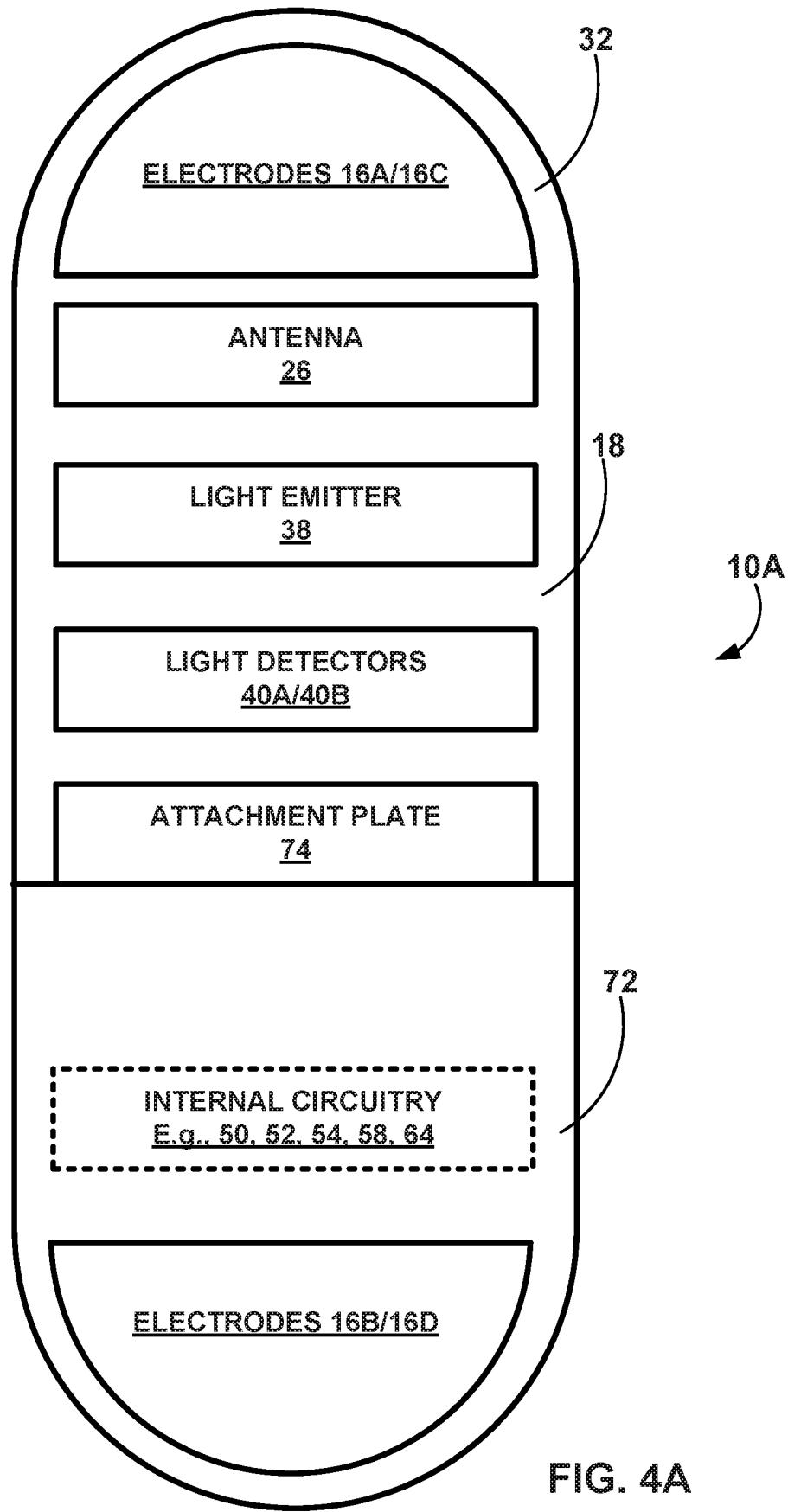

FIGS. 2-4B illustrate various aspects and example arrangements of IMD 10 of FIG. 1. For example, FIG. 2 conceptually illustrates an example physical configuration of IMD 10. FIG. 3 is a block diagram illustrating an example functional configuration of IMD 10. FIGS. 4A and 4B illustrate additional views of an example physical and functional configuration of IMD 10. It should be understood that any of the examples of IMD 10 described below with respect to FIGS. 2-4B may be used to implement the techniques described herein for determining a falling risk of patient 4.

FIG. 2 is a conceptual drawing illustrating an example configuration of IMD 10 of FIG. 1. In the example shown in FIG. 2, IMD 10 may comprise a leadless, subcutaneously-implantable monitoring device having housing 14, proximal electrode 16A, and distal electrode 16B. Housing 14 may further comprise first major surface 18, second major surface 20, proximal end 22, and distal end 24. In some examples, IMD 10 may include one or more additional electrodes 16C, 16D positioned on one or both of major surfaces 18, 20 of IMD 10. Housing 14 encloses electronic circuitry located inside the IMD 10, and protects the circuitry contained therein from fluids such as body fluids. In some examples, electrical feedthroughs provide electrical connection of electrodes 16A-16D, and antenna 26, to circuitry within housing 14. In some examples, electrode 16B may be formed from an uninsulated portion of conductive housing 14.

In the example shown in FIG. 2, IMD 10 is defined by a length L, a width W, and thickness or depth D. In this example, IMD 10 is in the form of an elongated rectangular prism in which length L is significantly greater than width W, and in which width W is greater than depth D. However, other configurations of IMD 10 are contemplated, such as those in which the relative proportions of length L, width W, and depth D vary from those described and shown in FIG. 2. In some examples, the geometry of the IMD 10, such as the width W being greater than the depth D, may be selected to allow IMD 10 to be inserted under the skin of the patient using a minimally invasive procedure and to remain in the desired orientation during insertion. In addition, IMD 10 may include radial asymmetries (e.g., the rectangular shape) along a longitudinal axis of IMD 10, which may help maintain the device in a desired orientation following implantation.

In some examples, a spacing between proximal electrode 16A and distal electrode 16B may range from about 30-55 mm, about 35-55 mm, or about 40-55 mm, or more generally from about 25-60 mm. Overall, IMD 10 may have a length L of about 20-30 mm, about 40-60 mm, or about 45-60 mm. In some examples, the width W of major surface 18 may range from about 3-10 mm, and may be any single width or range of widths between about 3-10 mm. In some examples, a depth D of IMD 10 may range from about 2-9 mm. In other examples, the depth D of IMD 10 may range from about 2-5 mm, and may be any single or range of depths from about 2-9 mm. In any such examples, IMD 10 is sufficiently compact to be implanted within the subcutaneous space of patient 4 in the region of a pectoral muscle.

IMD 10, according to an example of the present disclosure, may have a geometry and size designed for ease of implant and patient comfort. Examples of IMD 10 described in this disclosure may have a volume of 3 cubic centimeters (cm3) or less, 1.5 cm3 or less, or any volume therebetween. In addition, in the example shown in FIG. 2, proximal end 22 and distal end 24 are rounded to reduce discomfort and irritation to surrounding tissue once implanted under the skin of patient 4.

In the example shown in FIG. 2, first major surface 18 of IMD 10 faces outward towards the skin, when IMD 10 is inserted within patient 4, whereas second major surface 20 is faces inward toward musculature of patient 4. Thus, first and second major surfaces 18, 20 may face in directions along a sagittal axis of patient 4 (see FIG. 1), and this orientation may be maintained upon implantation due to the dimensions of IMD 10.

Proximal electrode 16A and distal electrode 16B may be used to sense cardiac EGM signals (e.g., ECG signals) when IMD 10 is implanted subcutaneously in patient 4. In the techniques described herein, processing circuitry of IMD 10 may determine a PTT value based in part on cardiac ECG signals, as further described below. The cardiac ECG signals may be stored in a memory of the IMD 10, and data derived from the cardiac ECG signals may be transmitted via integrated antenna 26 to another medical device, such as external device 12.

In the example shown in FIG. 2, proximal electrode 16A is in close proximity to proximal end 22, and distal electrode 16B is in close proximity to distal end 24 of IMD 10. In this example, distal electrode 16B is not limited to a flattened, outward facing surface, but may extend from first major surface 18, around rounded edges 28 or end surface 30, and onto the second major surface 20 in a three-dimensional curved configuration. As illustrated, proximal electrode 16A is located on first major surface 18 and is substantially flat and outward facing. However, in other examples not shown here, proximal electrode 16A and distal electrode 16B both may be configured like proximal electrode 16A shown in FIG. 2, or both may be configured like distal electrode 16B shown in FIG. 2. In some examples, additional electrodes 16C and 16D may be positioned on one or both of first major surface 18 and second major surface 20, such that a total of four electrodes are included on IMD 10. Any of electrodes 16A-16D may be formed of a biocompatible conductive material. For example, any of electrodes 16A-16D may be formed from any of stainless steel, titanium, platinum, iridium, or alloys thereof. In addition, electrodes of IMD 10 may be coated with a material such as titanium nitride or fractal titanium nitride, although other suitable materials and coatings for such electrodes may be used.

In the example shown in FIG. 2, proximal end 22 of IMD 10 includes header assembly 32 having one or more of proximal electrode 16A, integrated antenna 26, anti-migration projections 34, and suture hole 36. Integrated antenna 26 is located on the same major surface (e.g., first major surface 18) as proximal electrode 16A, and may be an integral part of header assembly 32. In other examples, integrated antenna 26 may be formed on the major surface opposite from proximal electrode 16A, or, in still other examples, may be incorporated within housing 14 of IMD 10. Antenna 26 may be configured to transmit or receive electromagnetic signals for communication. For example, antenna 26 may be configured to transmit to or receive signals from a programmer via inductive coupling, electromagnetic coupling, tissue conductance, Near Field Communication (NFC), Radio Frequency Identification (RFID), Bluetooth®, wireless local area network, or other proprietary or non-proprietary wireless telemetry communication schemes. Antenna 26 may be coupled to communication circuitry of IMD 10, which may drive antenna 26 to transmit signals to external device 12, and may transmit signals received from external device 12 to processing circuitry of IMD 10 via communication circuitry.

IMD 10 may include several features for retaining IMD 10 in position once subcutaneously implanted in patient 4. For example, as shown in FIG. 2, housing 14 may include anti-migration projections 34 positioned adjacent integrated antenna 26. Anti-migration projections 34 may comprise a plurality of bumps or protrusions extending away from first major surface 18, and may help prevent longitudinal movement of IMD 10 after implantation in patient 4. In other examples, anti-migration projections 34 may be located on the opposite major surface as proximal electrode 16A and/or integrated antenna 26. In addition, in the example shown in FIG. 2 header assembly 32 includes suture hole 36, which provides another means of securing IMD 10 to the patient to prevent movement following insertion. In the example shown, suture hole 36 is located adjacent to proximal electrode 16A. In some examples, header assembly 32 may comprise a molded header assembly made from a polymeric or plastic material, which may be integrated or separable from the main portion of IMD 10.

IMD 10 may determine values of PTTs of patient 4 based on signals received from one or more of electrodes 16A-16D, light emitter 38, and light detectors 40A, 40B. Electrodes 16A and 16B may be used to sense cardiac ECG signals for PTT value determination, as described herein. Additional electrodes 16C and 16D may be used to sense subcutaneous tissue impedance (e.g., for measuring PTT), in addition to or instead of electrodes 16A, 16B, in some examples.

In some examples, processing circuitry of IMD 10 may determine a PTT value of patient 4 prior to and after a Sit-to-Stand transition based on the sensed ECG signal from electrodes 16A, 16B and a current subcutaneous tissue impedance based on signals received from electrodes 16C and 16D. For example, the processing circuitry of IMD 10 may receive the ECG signal from electrodes 16A, 16B, and identify one or more features of a cardiac cycle within the ECG signal. For example, the processing circuitry may identify an R wave within a cardiac cycle, and associate a first time (T1) with the occurrence of the R wave. Next, the processing circuitry may identify a fluctuation in the subcutaneous tissue impedance signal occurring after T1, and associate a second time (T2) with the fluctuation, which may represent the passing of blood ejected during the observed cardiac cycle through the portion of the vasculature near electrodes 16C, 16D. By subtracting T2 from T1, processing circuitry of IMD 10 then may determine a PTT value (e.g., in milliseconds) of patient 4. To enable IMD 10 to accurately identify fluctuations in PTT values of patient 4, it may be beneficial for a clinician to implant IMD 10 substantially as shown in FIG. 1, with at least a portion of IMD 10 positioned at or inferior to heart 6 and subcutaneously or otherwise not adjacent to a central arterial blood flow. In this way, IMD 10 may be positioned at a sufficient circulatory distance from heart 6 to detect even small fluctuations in PTT, which may help IMD 10 to accurately assess the falling risk of patient 4.

In the example shown in FIG. 2, IMD 10 includes a light emitter 38, a proximal light detector 40A, and a distal light detector 40B positioned on housing 14 of IMD 10. Light detector 40A may be positioned at a distance S from light emitter 38, and a distal light detector 40B positioned at a distance S+N from light emitter 38. In other examples, IMD 10 may include only one of light detectors 40A, 40B, or may include additional light emitters and/or additional light detectors. Collectively, light emitter 38 and light detectors 40A, 40B may comprise an optical sensor, which may be used in the techniques described herein to determine PTT values of patient 4. Although light emitter 38 and light detectors 40A, 40B are described herein as being positioned on housing 14 of IMD 10, in other examples, one or more of light emitter 38 and light detectors 40A, 40B may be positioned, on a housing of another type of IMD within patient 4, such as a transvenous, subcutaneous, or extravascular pacemaker or ICD, or connected to such a device via a lead. Light emitter 38 includes a light source, such as an LED, that may emit light at one or more wavelengths within the (VIS) and/or (NIR) spectra. For example, light emitter 38 may emit light at one or more of about 660 (nm), 720 nm, 760 nm, 800 nm, or at any other suitable wavelengths.

As shown in FIG. 2, light emitter 38 may be positioned on header assembly 32, although, in other examples, one or both of light detectors 40A, 40B may additionally or alternatively be positioned on header assembly 32. In some examples, light emitter 38 may be positioned on a medial section of IMD 10, such as part way between proximal end 22 and distal end 24. Although light emitter 38 and light detectors 40A, 40B are illustrated as being positioned on first major surface 18, light emitter 38 and light detectors 40A, 40B alternatively may be positioned on second major surface 20. In some examples, IMD may be implanted such that light emitter 38 and light detectors 40A, 40B face inward when IMD 10 is implanted, toward the muscle of patient 4, which may help minimize interference from background light coming from outside the body of patient 4. Light detectors 40A, 40B may include a glass or sapphire window, such as described below with respect to FIG. 4B, or may be positioned beneath a portion of housing 14 of IMD 10 that is made of glass or sapphire, or otherwise transparent or translucent.

As noted above, light emitter 38 and one or both of light detectors 40A, 40B may be used in a technique for determining a PTT value of patient 4. As with techniques for determining PTT in which processing circuitry of IMD 10 receives a subcutaneous tissue impedance signal from a plurality of electrodes 16A-16D, techniques for determining PTT that include using an optical sensor include identifying one or more features within a cardiac cycle of patient 4, and associating a first time T1 with an occurrence in the cardiac cycle. Instead of determining a second time T2 based on an impedance signal, however, IMD 10 may determine T2 by identifying a fluctuation in the intensity and/or wavelength of light detected by one or both of light detectors 40A, 40B occurring after T1, and associate the second time (T2) with the fluctuation, which may represent the passing of blood ejected during the cardiac cycle through the portion of the vasculature near the light detectors 40A, 40B. By subtracting T2 from T1, processing circuitry of IMD 10 then may determine a PTT value (e.g., in milliseconds) of patient 4.

In some examples, IMD 10 may include one or more additional sensors, such as one or more accelerometers 64.

Such accelerometers 64 may be 3D accelerometers configured to generate signals indicative of one or more types of movement of the patient, such as gross body movement (e.g., activity) of the patient, patient posture, movements associated with the beating of the heart, or coughing, rales, or other respiration abnormalities. In some examples, one or more of such accelerometers may be used, in conjunction with light emitter 38 and optical detectors 40A, 40B, to determine a ballistocardiogram (i.e., a measure of motion corresponding to blood ejection at systole) that processing circuitry of IMD 10 may use to determine PTT instead of or in addition to an ECG signal from a pair of electrodes 16A-16D. IMD 10 may also monitor accelerometer signal(s) to determine that patient 4 has made a Sit-to-Stand transition. IMD 10 may also monitor accelerometer signal(s) to determine whether patient 4 is active. IMD 10 may determine the PTT of patient 4 prior to and after the Sit-to-Stand transition, may determine difference metrics between the PTT of patient 4 prior to and the PTT after the Sit-to-Stand transition, and may determine if a value of the difference metrics exceeds a threshold which may be indicative of an increase in the likelihood that patient 4 may fall.

Although processing circuitry of IMD 10 is described above as being configured to receive signals from one or more accelerometers, electrodes 16A-16D, light emitter 38, and/or light detectors 40A, 40B of IMD 10 and determine a value of one or more parameters of patient 4 based on such signals, any steps described herein as being carried out by processing circuitry of IMD 10 may carried out by processing circuitry of one or more devices. For example, processing circuitry of external device 12, or any other suitable implantable or external device or server, may be configured to receive signals from the one or more accelerometers, electrodes 16A-16D, light emitter 38, and/or light detectors 40A, 40B of IMD 10, such as via communication circuitry of IMD 10.

FIG. 3 is a functional block diagram illustrating an example configuration of IMD 10 of FIGS. 1 and 2. In the illustrated example, IMD 10 includes processing circuitry 50, sensing circuitry 52, communication circuitry 54, memory 56, switching circuitry 58, sensors 62, one or more accelerometers 64, in addition to previously-described electrodes 16A-16D, one or more of which may be disposed within housing 14 of IMD 10, and light emitter 38. In some examples, memory 56 includes computer-readable instructions that, when executed by processing circuitry 50, cause IMD 10 and processing circuitry 50 to perform various functions attributed to IMD 10 and processing circuitry 50 herein. Memory 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

As illustrated in FIG. 3, memory 56 also may include one or more tables 70 for storing baseline and threshold level values. As described above, in some examples, processing circuitry 50 of IMD 10 may be configured to determine baseline values of PTT differences during a learning phase of IMD 10, which then may be stored in tables 70. In addition, tables 70 may include pre-programmed baseline values that a clinician may select for patient 4 during setup of IMD 10, or baseline values that a clinician may manually enter based on the clinician's assessments of patient 4. Processing circuitry 50 also may be configured to determine threshold values for deviations of difference values of PTT from the baseline values, and store the threshold values in tables 70. In some examples, processing circuitry 50 may determine such threshold values based, at least in part, on baseline values selected for patient 4. In addition to the baseline values, tables 70 may include threshold values that a clinician may select for patient 4 during setup of IMD 10, or threshold values that a clinician may manually enter based on the clinician's assessments of patient 4.

Sensing circuitry 52 and communication circuitry 54 may be selectively coupled to electrodes 16A-16D via switching circuitry 58, as controlled by processing circuitry 50. Sensing circuitry 52 may monitor signals from electrodes 16A-16D in order to monitor electrical activity of heart (e.g., to produce an ECG for PTT determination), and/or subcutaneous tissue impedance Z (e.g., for PTT determination). Sensing circuitry 52 also may monitor signals from sensors 62, which may include light detectors 40A, 40B, and any additional light detectors that may be positioned on IMD 10. In some examples, sensing circuitry 52 may include one or more filters and amplifiers for filtering and amplifying signals received from one or more of electrodes 16A-16D and/or light detectors 40A, 40B.

In some examples, processing circuitry 50 also may include a rectifier, filter and/or amplifier, a sense amplifier, comparator, and/or analog-to-digital converter. Upon receiving signals from electrodes 16A-16D and light detectors 40A, 40B via sensing circuitry 52, processing circuitry 50 may determine PTT for patient 4. Processing circuitry then may compare the PTT to the baseline levels stored in tables 70, and determine whether differences between the current values and the corresponding baseline levels satisfy corresponding thresholds stored in tables 70.

Processing circuitry 50 may store the determined values in difference metrics/slopes 68 of memory 56, along with an indication of a date and time of the measurements. Simultaneously or thereafter, processing circuitry 50 may transmit, via communication circuitry 54 an indication that patient 4 is more likely to fall to external device 12.

Communication circuitry 54 may include any suitable hardware, firmware, software or any combination thereof for communicating with another device, such as external device 12 or another IMD or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., antenna 26. In some examples, communication circuitry 54 may communicate with external device 12. In addition, processing circuitry 50 may communicate with a networked computing device via external device (e.g., external device 12) and a computer network, such as the Medtronic CareLink® Network developed by Medtronic, plc, of Dublin, Ireland.

A clinician or other user may retrieve data from IMD 10 using external device 12, or by using another local or networked computing device configured to communicate with processing circuitry 50 via communication circuitry 54. The clinician may also program parameters of IMD 10 using external device 12 or another local or networked computing device. In some examples, the clinician may select baseline values and threshold values.

The various components of IMD 10 may be coupled a power source, which may include a rechargeable or non-rechargeable battery positioned within housing 14 of IMD 10. A non-rechargeable battery may be selected to last for several years, while a rechargeable battery may be inductively charged from an external device, e.g., on a daily or weekly basis.

FIGS. 4A and 4B illustrate two additional example IMDs that may be substantially similar to IMD 10 of FIGS. 1-3, but which may include one or more additional features. The components of FIGS. 4A and 4B may not necessarily be drawn to scale, but instead may be enlarged to show detail. FIG. 4A is a block diagram of a top view of an example configuration of an IMD 10A. FIG. 4B is a block diagram of a side view of example IMD 10B, which may include an insulative layer as described below.

FIG. 4A is a conceptual drawing illustrating another example IMD 10A that may be substantially similar to IMD 10 of FIG. 1. In addition to the components illustrated in FIGS. 1-3, the example of IMD 10 illustrated in FIG. 4A also may include a body portion 72 and an attachment plate 74. Attachment plate 74 may be configured to mechanically couple header 32 to body portion 72 of IMD 10A. Body portion 72 of IMD 10A may be configured to house one or more of the internal components of IMD 10 illustrated in FIG. 3, such as one or more of processing circuitry 50, sensing circuitry 52, communication circuitry 54, memory 56, switching circuitry 58, internal components of sensors 62, and one or more accelerometers 64. In some examples, body portion 72 may be formed of one or more of titanium, ceramic, or any other suitable biocompatible materials.

FIG. 4B is a conceptual drawing illustrating another example IMD 10B that may include components substantially similar to IMD 10 of FIG. 1. In addition to the components illustrated in FIGS. 1-3, the example of IMD 10B illustrated in FIG. 4B also may include a wafer-scale insulative cover 76, which may help insulate electrical signals passing between electrodes 16A-16D and/or optical detectors 40A, 40B on housing 14B and processing circuitry 50. In some examples, insulative cover 76 may be positioned over an open housing 14 to form the housing for the components of IMD 10B. One or more components of IMD 10B (e.g., antenna 26, light emitter 38, light detectors 40A, 40B, processing circuitry 50, sensing circuitry 52, communication circuitry 54, switching circuitry 58, and/or one or more accelerometers 64) may be formed on a bottom side of insulative cover 76, such as by using flip-chip technology. Insulative cover 76 may be flipped onto a housing 14B. When flipped and placed onto housing 14B, the components of IMD 10B formed on the bottom side of insulative cover 76 may be positioned in a gap 78 defined by housing 14B.

Insulative cover 76 may be configured so as not to interfere with the operation of IMD 10B. For example, one or more of electrodes 16A-16D may be formed or placed above or on top of insulative cover 76, and electrically connected to switching circuitry 58 through one or more vias (not shown) formed through insulative cover 76. In addition, to enable IMD 10B to determine values of PTT, at least a portion of insulative cover 76 may be transparent to the NIR or visible wavelengths emitted by light emitter 38 and detected by light detectors 40A, 40B, which in some examples may be positioned on a bottom side of insulative cover 76 as described above.

In some examples, light emitter 38 may include an optical filter between light emitter 38 and insulative cover 76, which may limit the spectrum of emitted light to be within a narrow band. Similarly, light detectors 40A, 40B may include optical filters between light detectors 40A, 40B and insulative cover 76, so that light detectors 40A, 40B detects light from a narrow spectrum, generally at longer wavelengths than the emitted spectrum. Other optical elements that may be included in the IMD 10B may include index matching layers, antireflective coatings, or optical barriers, which may be configured to block light emitted sideways by the light emitter 38 from reaching light detector 40.

Insulative cover 76 may be formed of sapphire (i.e., corundum), glass, parylene, and/or any other suitable insulating material. Sapphire may be greater than 80% transmissive for wavelengths in the range of about 300 nm to about 4000 nm, and may have a relatively flat profile. In the case of variation, different transmissions at different wavelengths may be compensated for, such as by using a ratiometric approach. In some examples, insulative cover 76 may have a thickness of about 300 micrometers to about 600 micrometers. Housing 14B may be formed from titanium or any other suitable material (e.g., a biocompatible material), and may have a thickness of about 200 micrometers to about 500 micrometers. These materials and dimensions are examples only, and other materials and other thicknesses are possible for devices of this disclosure.

Figure 5:
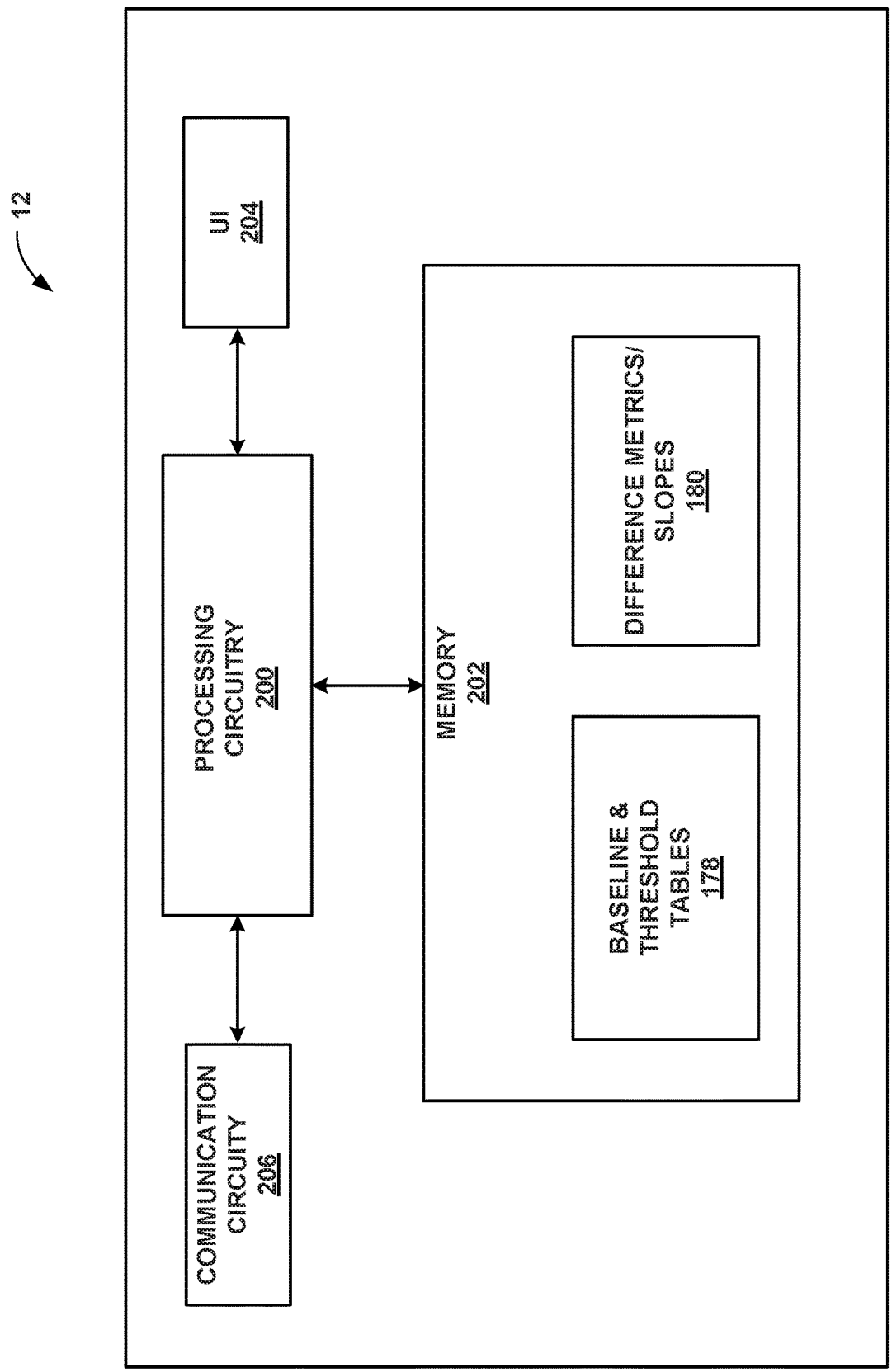
FIG. 5 is a block diagram illustrating an example external device.

FIG. 5 is a functional block diagram illustrating an example configuration of an external device 12 configured to communicate with one or more IMDs 10. In the example of FIG. 5, external device 12 includes processing circuitry 200, memory 202, user interface (UI) 204, and communication circuitry 206. External device 12 may correspond to any of external devices 12 described with respect to FIGS. 1 and 6. External device 12 may be a dedicated hardware device with dedicated software for the programming and/or interrogation of an IMD 10. Alternatively, external device 12 may be an off-the-shelf computing device, e.g., a smartphone running a mobile application that enables external device 12 to program and/or interrogate IMD 10. In some examples where external device 12 is a smart phone, external device 12 may include a mobile application to facilitate interaction with IMD 10.

In some examples, a user of external device 12 may be clinician, physician, heath care giver, patient, family member of the patient or friend of the patient. In some examples, a user uses external device 12 to select or program any of the values for operational parameters of IMD 10, e.g., for measuring or determining patient body stability based on PTT. In some examples, a user uses external device 12 to receive data collected by IMD 10, such as difference metrics/slopes 180 or other operational and performance data of IMD 10. The user may also receive alerts provided by IMD 10 that indicate that an acute cardiac event, e.g., ventricular tachyarrhythmia, is predicted. The user may also receive alerts that the patient may be more likely to fall or that the patient needs attention due to deterioration of the patient's body stability. The user may interact with external device 12 via UI 204, which may include a display to present a graphical user interface to a user, and a keypad or another mechanism (such as a touch sensitive screen) for receiving input from a user. External device 12 may communicate wirelessly with IMD 10 using communication circuitry 206, which may be configured for RF communication with communication circuitry 168 of IMD 10.

Processing circuitry 200 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 200 may include multiple components, such as any combination of one or more microprocessors, one or more DSPs, one or more ASICs, or one or more FPGAs, as well as other discrete or integrated logic circuitry, and/or analog circuitry.

Memory 202 may store program instructions, which may include one or more program modules, which are executable by processing circuitry 200. When executed by processing circuitry 200, such program instructions may cause processing circuitry 200 and external device 12 to provide the functionality ascribed to them herein. The program instructions may be embodied in software, firmware and/or RAMware. Memory 202 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In some examples, processing circuitry 200 of external device 12 may be configured to provide some or all of the functionality ascribed to processing circuitry 50 of IMD 10 herein. For example, processing circuitry 200 may receive physiological signals generated by one or more IMDs 10 and difference metrics/slopes 180 and/or may receive difference metrics/slopes 180 from one or more IMDs 10. Processing circuitry 200 may determine baselines stored in baseline & threshold tables 178 and/or difference metrics/slopes 180 in the manner described herein with respect to processing circuitry 50 of IMD 10 for determining patient body stability based on accelerometer-generated data.

Figure 6:
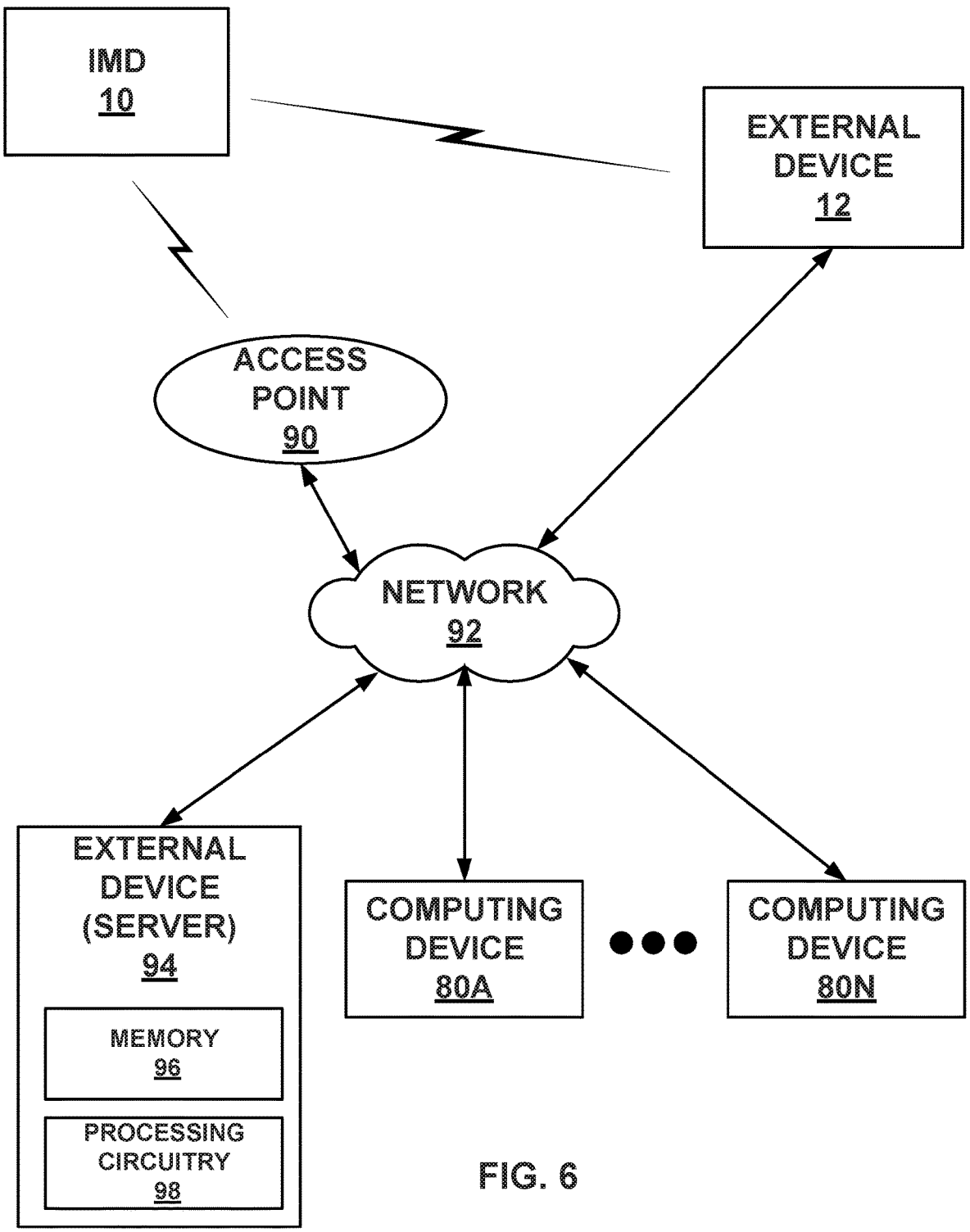
FIG. 6 is a block diagram illustrating an example system that includes an external device, such as a server, and one or more computing devices that are coupled to the leadless implantable medical device of FIG. 1 and the external device of FIG. 1 via a network.

FIG. 6 is a functional block diagram illustrating an example system that includes an access point 90, a network 92, external computing devices, such as a server 94, and one or more other computing devices 80A-80N, which may be coupled to IMD 10, and external device 12 via network 92. In this example, IMD 10 may use communication module 54 to communicate with external device 12 via a first wireless connection, and to communicate with an access point 90 via a second wireless connection. In the example of FIG. 6, access point 90, external device 12, server 94, and computing devices 80A-80N are interconnected and may communicate with each other through network 92.

Access point 90 may comprise a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. As discussed above, IMD 10 may be configured to transmit data, such as current values and falling risk, to external device 12. In addition, access point 90 may interrogate IMD 10, such as periodically or in response to a command from the patient or network 92, in order to retrieve values determined by processing circuitry 50 of IMD 10, or other operational or patient data from IMD 10. Access point 90 may then communicate the retrieved data to server 94 via network 92.

In some cases, server 94 may be configured to provide a secure storage site for data that has been collected from IMD 10, and/or external device 12. In some cases, server 94 may assemble data in web pages or other documents for viewing by trained professionals, such as clinicians, via computing devices 80A-80N. One or more aspects of the illustrated system of FIG. 6 may be implemented with general network technology and functionality, which may be similar to that provided by the Medtronic CareLink® Network developed by Medtronic plc, of Dublin, Ireland.

In some examples, one or more of computing devices 80A-80N (e.g., device 80A) may be a tablet or other smart device located with a clinician, by which the clinician may program, receive alerts from, and/or interrogate IMD 10. For example, the clinician may access patient 4's PTT measurements or difference metrics or slopes through device 80A, such as when patient 4 is in in between clinician visits, to check on a falling risk of patient 4 as desired. In some examples, the clinician may enter instructions for a medical intervention for patient 4 into an app in device 80A, such as based on falling risk of patient 4 determined by IMD 10, or based on other patient data known to the clinician. Device 80A then may transmit the instructions for medical intervention to another of computing devices 80A-80N (e.g., device 80B) located with patient 4 or a caregiver of patient 4. For example, such instructions for medical intervention may include an instruction to change a drug dosage, timing, or selection, to schedule a visit with the clinician, or to seek medical attention. In further examples, device 80B may generate an alert to patient 4 based on a falling risk of patient 4 determined by IMD 10, which may enable patient 4 proactively to seek medical attention prior to receiving instructions for a medical intervention. In this manner, patient 4 may be empowered to take action, as needed, to address his or her falling risk, which may help improve clinical outcomes for patient 4.

Figure 7:
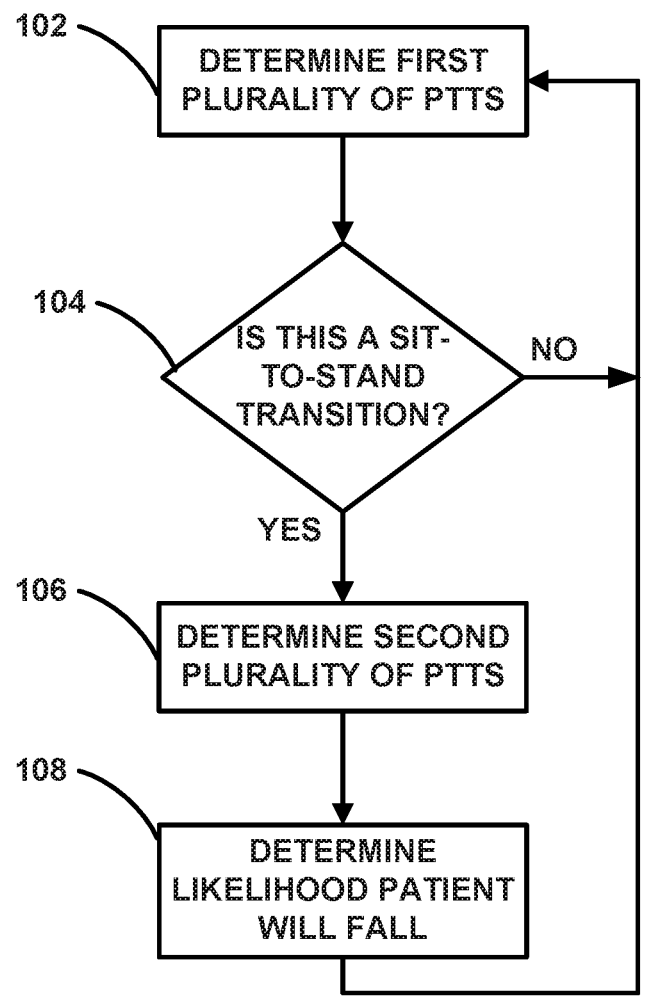
FIG. 7 is a flow diagram illustrating an example technique for determining a likelihood of a patient to fall.

FIG. 7 is a flow diagram illustrating an example technique for determining a likelihood of a patient to fall. As described herein, the techniques illustrated in FIG. 7 may be employed using one or more components of system 2, which have been described above with respect to FIGS. 1-5. Although described as being performed by IMD 10, the techniques of FIG. 7 may be performed, in whole or in part, by processing circuitry and memory of other devices of a medical device system, as described herein. For example, although processing circuitry 50 of IMD is described as carrying out most of the example techniques illustrated in FIG. 7 for the sake of clarity, in other examples, one or more devices (e.g., external device 12 or other external device or server) or a clinician may carry out one or more steps attributed below to processing circuitry 50 of IMD 10.

The example of FIG. 7 may be an example technique for determining, by processing circuitry 50 of IMD 10, body stability or a falling risk of patient 4 based on a comparison of difference metrics or slopes based on PTT values of patient 4 to corresponding baseline values stored in tables 70 of memory 56. As discussed above, IMD 10 may determine baseline PTT values for patient 4. In some examples, IMD 10 may determine the baseline values during a learning phase of IMD 10 following implantation of IMD 10 into patient 4, as discussed above with respect to FIG. 1. Such a learning phase may take place after implantation of IMD 10 at a time when the condition of patient 4 is stable.

Processing circuitry 50 may determine a first plurality of PTTs of patient 4 prior to a Sit-to-Stand transition of patient 4 (102), for example, through the use of sensors as described above. The first plurality of PTTs may be PTTs measured prior to a Sit-to-Stand transition and may be stored in rolling buffer 63, for example. Processing circuitry 50 may determine, based on at least one accelerometer signal, whether a Sit-to-Stand transition occurs (104). For example, processing circuitry 50 may monitor signals of one or more accelerometers 64 to determine whether a Sit-to-Stand transition has occurred. Details on how to determine a Sit-to-Stand transition is occurring based on an accelerometer signal can be found in commonly-assigned U.S. patent application Ser. No. 15/607,945, titled, "ACCELEROMETER SIGNAL CHANGE AS A MEASURE OF PATIENT FUNCTIONAL STATUS," filed May 25, 2017, now published as US Patent Application Publication No. US 2018/0035924 A1 and claiming the benefit of Provisional Application No. 62/370, 138, filed on Aug. 2, 2016, the entire content of which is incorporated by reference herein.

If a Sit-to-Stand transition has not occurred (the "NO" path in FIG. 7), processing circuitry may continue to determine the first plurality of PTTs (102). In some examples, if a Sit-to-Stand transition has occurred, processing circuitry 50 may determine whether patient 4 has been inactive for a predetermined period of time. Processing circuitry 50 may make this determination based on a signal from an activity sensor. In some examples, the activity sensor is an accelerometer within IMD 10 or whichever medical device is performing the techniques of this disclosure. In some examples, processing circuitry 50 determines a number of activity counts based on one or more accelerometer signals exceeding one or more thresholds and uses the number of activity counts to determine if the patient has been inactive for the predetermined period of time. The activity counts used to determine if the patient has been inactive for the predetermined period of time may be a total, mean, or median number of counts during the period. In some examples, IMD 10 may determine if patient 14 has been inactive by determining patient 14 has not taken a step by monitoring the accelerometer signal for an indication that a step has been taken. Details on how to determine when a step is taken based on an accelerometer signal can be found in commonly-assigned U.S. patent application Ser. No. 15/603, 776, titled, "STEP DETECTION USING ACCELEROMETER AXIS," filed May 24, 2017, now published as US Patent Application Publication No. US 2018/0035920 A1 and claiming the benefit of Provisional Application No. 62/370,102, filed on Aug. 2, 2016, the entire content of which is incorporated by reference herein.

In some examples, if IMD 10 does not determine that patient 4 has been inactive for at least a predetermined period of time prior to the Sit-to-Stand transition (e.g., patient 4 has been active), in some examples, IMD 10 may ignore the Sit-to-Stand transition and continue to determine the first plurality of PTTs (102). The predetermined period of time may be programmable by external device 12 for example, or may be fixed. In some examples, the predetermined period of time may be several minutes, such as six minutes. IMD 10 may ignore the Sit-to-Stand transition shortly after a period in which patient 4 is active because recent activity may decrease the likelihood of patient 4's body stability being worse than normal or the measurement of the PTTs prior to and after the Sit-to-Stand transition may not be as comparable with other measurements due to the measurements after recent activity may not be consistent with measurements during less active times. By ignoring the Sit-to-Stand transition shortly after a period in which patient 4 is active, IMD 10 may save battery power and may preserve a data set of PTTs prior to and after Sit-to-Stand transitions that is more indicative of a measure of body stability issues. Alternatively, ICM 10B may not determine if patient 14 has been inactive for a predetermined period of time prior to the Sit-to-Stand transition.

In some examples, if a Sit-to-Stand transition has occurred (the "YES" path in FIG. 7), processing circuitry 50 may determine, based on the Sit-to-Stand transition occurring, a second plurality of PTTs after the Sit-to-Stand transition of patient 4 (106). For example, the processing circuitry 50 may measure the second plurality of PTTs after the Sit-to-Stand transition and may store the second plurality of PTTs in rolling buffer 63.

Processing circuitry 50 may determine a likelihood the patient will fall based on the first plurality of PTTs and the second plurality of PTTs (108). For example, processing circuitry 50 may determine the likelihood patient 4 will fall at least in part by calculating a first metric based on the first plurality of PTTs (PTTs prior to a Sit-to-Stand transition). The first metric may include, for example, a median, mean or mode of PTTs prior to a Sit-to-Stand transition. Processing circuitry 50 of IMD 10 may further determine the likelihood patient 4 will fall at least in part by calculating second metrics based on the second plurality of PTTs (e.g., PTTs after each Sit-to-Stand transition). For example, the second metrics may include at least one of a slope of the second plurality of PTTs, a minimum pulse transit time of the second plurality of PTTs, a maximum PTT of the second plurality of PTTs, or a median, mean, or mode of the second plurality of PTTs. The second metrics may therefore include a slope of the second plurality of PTTs, a minimum PTT after the Sit-to-Stand transition (e.g., the fastest PTT), a maximum PTT after the Sit-to-Stand transition (e.g., the slowest PTT), and/or a median, mean or mode of PTTs after the Sit-to-Stand transition.

In some examples, processing circuitry 50 may determine the likelihood the patient will fall at least in part by calculating difference metrics. The difference metrics may include at least one of a difference between the first metric and one or more of the second metrics. For example, the difference metrics may include at least one of a difference between the first metric and a minimum PTT of the second plurality of PTTs, a difference between the first metric and a maximum PTT of the second plurality of PTTs, or a difference between the first metric and a median, mean or mode of the second plurality of PTTs. For example, processing circuitry 50 of IMD 10 may calculate a minimum difference, a maximum difference and a median, mean or mode difference by subtracting each of the second metrics (e.g., from the second plurality of PTTs after the Sit-to-Stand transition) from the first metric (e.g., the mean, median or mode of the first PTTs prior to the Sit-to-Stand transition). For example, processing circuitry 50 of IMD 10 may calculate MinDiff by subtracting the fastest Sit-to-Stand transition PTT from the median of the pre-Sit-to Stand transition PTTs. Processing circuitry 50 may calculate MaxDiff by subtracting the slowest post Sit-to-Stand transition PTT from the median of the pre-Sit-to Stand transition PTTs. Processing circuitry may also calculate MedDiff by subtracting the median post Sit-to-Stand transition PTT from the median of the pre-Sit-to Stand transition PTTs.

Processing circuitry 50 of IMD 10 may, in addition to or in place of the difference metrics, calculate the slope of the PTT values after the Sit-to-Stand transition (110). IMD 10 may track the slope of the PTT values after the Sit-to-Stand transition and the difference metrics over time, for example, by storing calculated difference metrics and slope values in difference metrics/slopes 68 in memory 56. In some examples, IMD 10 may use the difference metrics and/or the slope of the PTT values after the Sit-to-Stand transition to update the baseline(s) in table 70. An acute or chronic change in these metrics may be an indication that patient 4 is becoming more likely to fall upon standing. Processing circuitry 50 may store the difference metrics and the slope of the PTT values after the Sit-to-Stand transition in memory 56.

In some examples, processing circuitry 50 of IMD 10 may determine the likelihood patient 4 will fall at least in part by calculating tendency metrics 71 based on at least one of the difference metrics of the slope of the second plurality of PTTs (e.g., the PTTs after the Sit-to-Stand transition) over time. For example, processing circuitry 50 may calculate tendency metrics 71 based upon at least one of the difference metrics or the slope of the second plurality of PTTs over time. For example, processing circuitry 50 may periodically (e.g., daily) calculate tendency metrics 71. For example, processing circuitry 50 of IMD 10 may calculate a central tendency (such as a median, mean or mode) of one or more of the difference metrics and/or slope of the PTTs after the Sit-to-Stand transitions and a variability (such as a standard deviation or interquartile range) of one or more of the difference metrics and/or slope of the PTTs after the Sit-to-Stand transitions. In other examples, processing circuitry 50 of IMD 10 may calculate tendency metrics 71 based upon a user request on external device 12. For example, processing circuitry 50 of IMD 10 may calculate a central tendency (such as a median, mean or mode) of one or more of the difference metrics and/or the slope of the PTTs after the Sit-to-Stand transitions and a variability (such as a standard deviation or interquartile range) of one or more of the difference metrics and/or the slope of the PTTs after the Sit-to-Stand transitions based upon a user request on external device 12. Processing circuitry 50 may store the tendency metrics 71 (e.g., central tendencies and/or the variabilities) in memory 56. In some examples, the tendency metrics may be stored as baseline values. In some examples, processing circuitry 50 may determine the likelihood the patient will fall at least in part by comparing at least one of the difference metrics or the slope of the second plurality of PTTs to past tendency metrics.

IMD 10 may measure PTT on a periodic basis such as every minute. IMD 10 may then store the resulting measurements in rolling buffer 63. Rolling buffer 63 may be configured to store a predetermined number of PTT values. For example, the rolling buffer may be configured to store 12 PTT values.

In the example where the rolling buffer is configured to store 12 PTT values, processing circuitry 50 of IMD 10 may calculate a median, mean or mode of first five PTT measurements in the rolling buffer (those associated with patient 4 sitting). In some examples, processing circuitry 50 may ignore PTT measurements that may occur during the Sit-to-Stand transition, for example the middle two values in the rolling buffer. Processing circuitry 50 may continue to calculate PTT an additional five times after standing for example and calculate slope of the PTT values post-standing, the minimum PTT value post-standing, the maximum PTT value post-standing, and the median, mean or mode PTT value post-standing. Processing circuitry 50 of IMD 10 may then calculate the difference metrics, such as the difference between the post-standing metrics and the mean, median or mode of the pre-standing (e.g., sitting) PTT.

Processing circuitry 50 of IMD 10 may compare the difference metrics and/or the slope of the PTT values post-standing with baseline metrics saved in tables 70 to determine if the body of patient 4 may be less stable than at a time when the baseline was determined. IMD 10 may send an alert to external device 12, for example, if it determines that there is an acute or chronic change in the difference metrics and/or the slope of the PTT values post-standing. For example, communication circuitry 54 may be configured to transmit an alert to an external device, such as external device 12, upon determining the likelihood the patient will fall has increased.

For example, if the difference metrics or the slope of the PTT values post-standing change by 50% within a relatively shorter time span, two days for instance, that may be indicative of an acute change in patient 4 body stability and a higher likelihood for a fall. If the difference metrics or the slope of the PTT values post-standing change over a relatively longer period of time, two weeks for instance, that may be indicative of a chronic change in patient 4 body stability and a higher likelihood of a fall.

In some examples, processing circuitry 50 also may determine whether a difference between one or more of the difference metrics and/or slope of the PTTs after the Sit-to-Stand transition and the corresponding baseline values satisfies a threshold value. In some examples, a threshold change value for a given parameter may be an absolute value of a percentage of the baseline value. For example, if a baseline value of a difference metric is=X, then a threshold value of the difference metric may be X±0.5X. IMB 10 may repeat steps 100-114 during each Sit-to-Stand transition.

Figure 8:
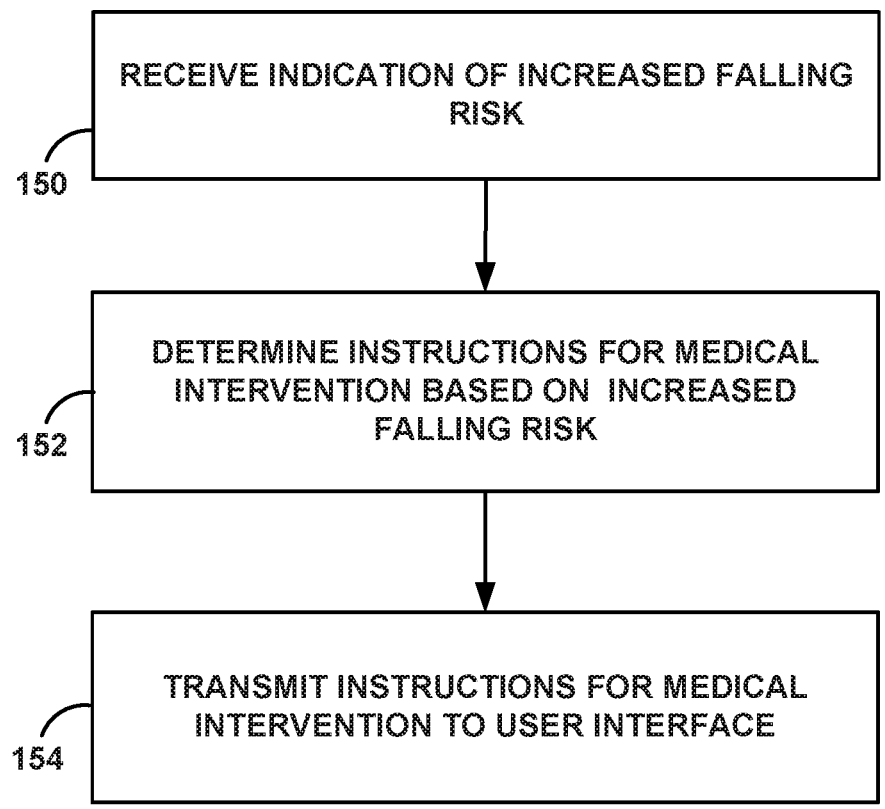
FIG. 8 is a flow diagram illustrating an example technique for an external device to determine instructions for a medical intervention based on a falling risk.

FIG. 8 is a flow diagram illustrating an example technique for external device 12 to determine instructions or treatment for a medical intervention based on a falling risk of patient 4 received from IMB 10, and transmit the instructions or treatment to a user interface. The method illustrated in FIG. 8 may be used with any of the methods for determining a falling risk by IMD 10 described herein, such as the method illustrated in FIG. 7. In the illustrated example, external device 12 is configured to receive a falling risk of patient 4 from IMB 10, which may be transmitted to a processing circuitry of external device 12 via communication circuitry 54 and antenna 26 of IMD 10 (150).

In some examples, upon receiving the falling risk of patient 4 from IMD 10 and prior to determining instructions or treatment for a medical intervention for patient 4, external device 12 may transmit one or more queries to a user device. For example, external device 12 may ask patient 4 or a caregiver to answer questions about recent or current activities or symptoms of patient 4, such as whether patient 4 recently has exercised, taken medications, or experienced symptoms. In addition, external device 12 may interrogate IMD 10 for difference metrics and/or the slope of PTTs after Sit-to-Stand transition(s) of patient 4, if IMD 10 did not already transmit the difference metrics to external device 12. Based on the falling risk of patient 4, and optionally based on answers to queries and/or the current values of patient 4, external device 12 then may determine instructions or treatment for a medical intervention for patient 4 (152).

In some examples, external device 12 may determine the instructions or treatment for medical intervention independent of clinician input, such as by selecting among treatment options stored in a memory of external device 12 or a centralized database that are associated with the falling risk of patient 4. In other examples, a clinician may determine the instructions or treatment for medical intervention on substantially the same basis, and input the instructions to external device 12. External device 12 then may transmit the instructions or treatment to an interface of the user device with patient 4 (154). In some examples, external device 12 may control IMD 10, for example, to deliver a treatment such as a stimulation to the heart or a nerve. In other examples, external device may control a drug pump to deliver a drug to patient 4. In some examples, external device 12 may transmit follow-up queries to patient 4 or a caregiver via the user device after transmitting the instructions. Such queries may include questions pertaining to patient 4's understanding of the transmitted instructions, whether patient 4 has complied with the instructed medical intervention, whether patient 4 feels their condition has improved and/or whether patient 4 is experiencing symptoms. External device 12 may store patient 4's responses in a memory of external device 12, or in a centralized database. A clinician may review the responses, and remotely follow-up with patient 4 as needed following any changes to patient 4's treatment. In this manner, the techniques and systems described herein advantageously may enable patient 4 to receive individualized, frequently updated treatment at less expense than a comparable number of clinician visits would incur. In addition, the techniques and systems may help reduce falling events for patient 4.

During the medical intervention, processing circuitry 50 of IMD 10 may continue to measure body stability or falling risk as discussed with respect to FIG. 7. In this manner, feedback may be provided to a clinician or patient 4 as to the efficacy of the medical intervention.

Although processing circuitry 50 of IMD 10 and processing circuitry of external device 12 is described above as being configured to perform one or more of the steps of the techniques illustrated in FIGS. 7-8, any steps of the techniques described herein may be performed by processing circuitry of the other of IMD 10 or external device 12, or by one or more other devices. For example, processing circuitry of external device 12, or of any other suitable implantable or external device or server, may be configured to perform one or more of the steps described as being performed by processing circuitry 50 of IMD 10. In other examples, processing circuitry 50 of IMD 10, or of any other suitable implantable or external device or server, may be configured to perform one or more of the steps described as being performed by processing circuitry of external device 12. Such other implantable or external devices may include, for example, an implantable pacemaker or ICD, an external monitoring device, or any other suitable device. In addition, although the optical sensors and electrodes are described herein as being positioned on a housing of IMD 10, in other examples, such optical sensors and/or electrodes may be positioned on a housing of another device implanted in or external to patient 4, such as a transvenous, subcutaneous, or extravascular pacemaker or ICD, or coupled to such a device by one or more leads.

Figure 9:
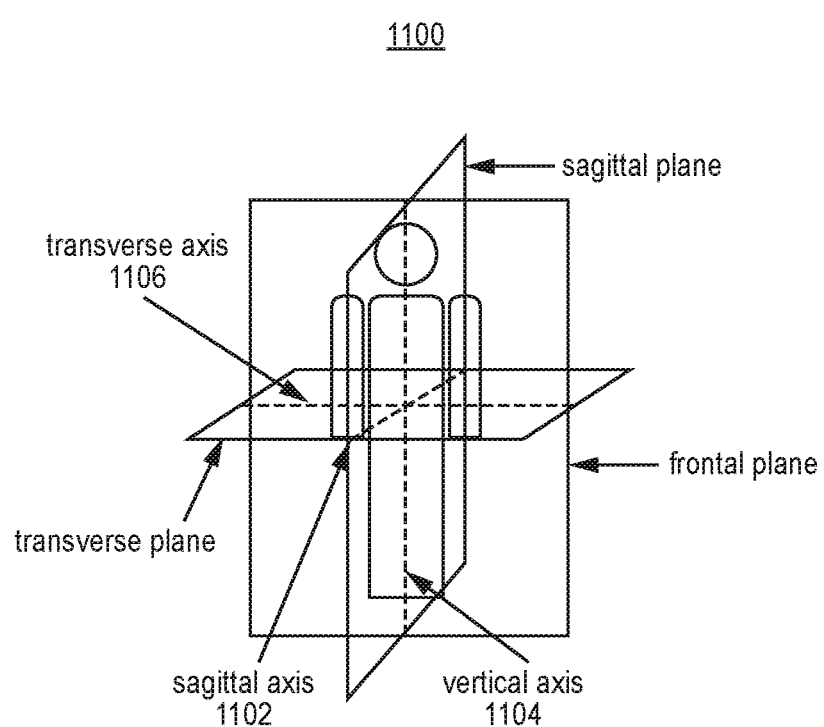
FIG. 9 is a conceptual diagram illustrating sagittal, vertical and transverse axes in a three-dimensional coordinate system.

FIG. 9 is a conceptual diagram 1100 illustrating a sagittal axis 1102, a vertical axis 1104 and transverse axis 1106 in a three-dimensional coordinate system. As can be seen, sagittal axis 1102 runs in the anterior-posterior direction, vertical axis 1104 runs vertically and transverse axis runs left-right.

Figure 10:
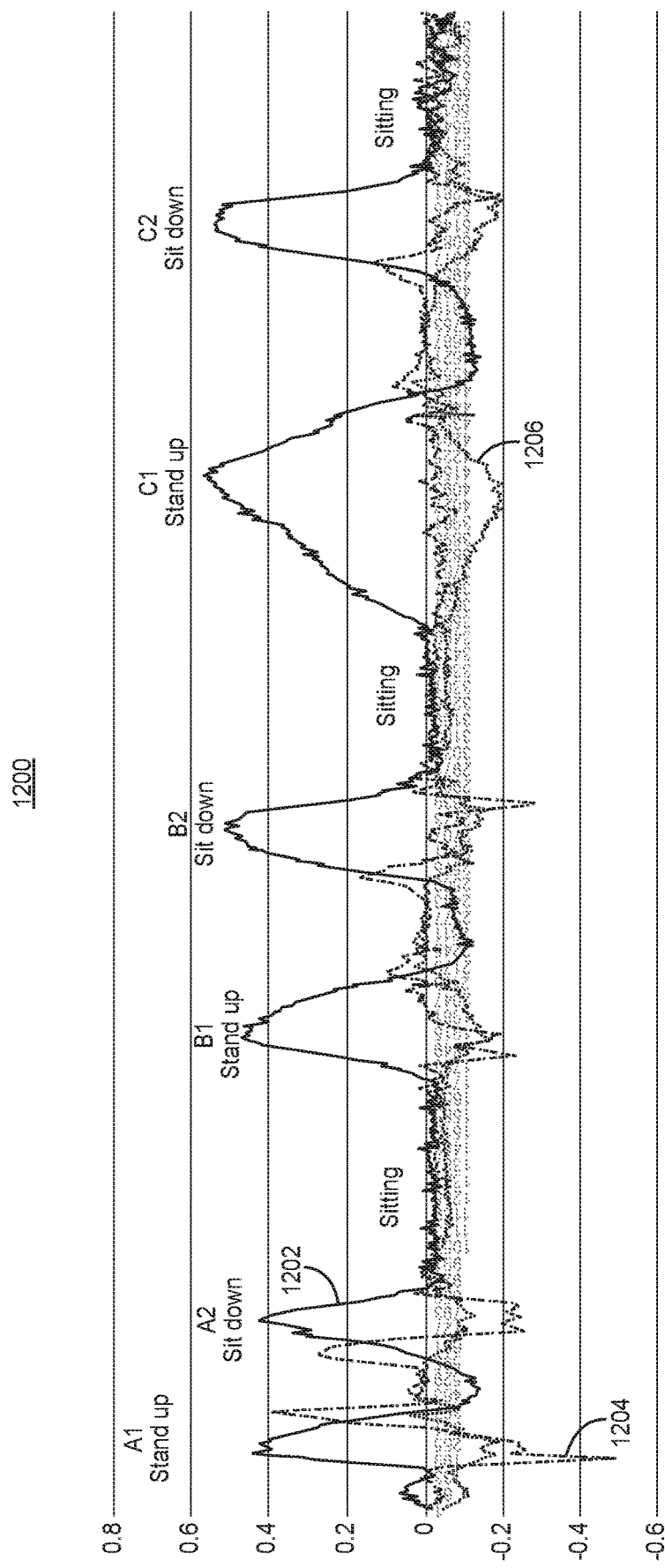
FIG. 10 is a plot illustrating sagittal, vertical and transverse axis signals produced by an accelerometer during a series of sit-stand and stand-sit movements.

FIG. 10 is a plot 1200 illustrating a sagittal axis signal 1202, a vertical axis signal 1204, and a transverse axis signal 1206 produced by an accelerometer (see e.g., FIG. 7, element 166) during a series of sit-stand and stand-sit movements labeled A1-A2, B1-B2 and C1-C2, respectively. The sagittal axis signal 1202 corresponds to the trace or trend that exhibits the largest amplitude variations primarily on the (+) side of the y-axis (arbitrary units) across each one of A1-A2, B1-B2 and C1-C2. The vertical axis signal 1204 corresponds to the trace or trend that exhibits moderate amplitude variations on the (+) side and the (−) side of the y-axis across each one of A1-A2, B1-B2 and C1-C2. The transverse axis signal 1206 corresponds to the trace or trend that exhibits amplitude variations primarily on the (−) side of the y-axis across each one of A1-A2, B1-B2 and C1-C2, exhibits a number of zero-crossings that is less than a number of zero-crossings of the vertical axis signal 1204.

The range of voltage variation provided within sagittal axis signal 1202, vertical axis signal 1204, and transverse axis signal 1206 is not limited to any particular range of voltage variation, and in some examples is the voltage variation of sagittal axis signal 1202, vertical axis signal 1204, and transverse axis signal 1206 as provided by the accelerometer configured to generated and provide the single axis accelerometer output signal processed to detect steps. In various examples, instead of sagittal axis signal 1202, a vertical axis signal 1204, and transverse axis signal 1206 showing variations in voltage relative to the vertical axis, the variations are scaled to represent variations in gravitational force, measured in units of gravity—e.g., gravity=9.80991 m/s2, and the variations in sagittal axis signal 1202, vertical axis signal 1204, and transverse axis signal 1206 represent variations, measured in units, in the gravitational forces exerted in the respective axis.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the terms "processor" or "processing circuitry" as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

The present disclosure includes the following examples.

Example 1. A system comprising: accelerometer circuitry configured to generate at least one signal; memory; and processing circuitry coupled to the accelerometer circuitry and the memory, the processing circuitry being configured to: determine a first plurality of pulse transit times of a patient prior to a Sit-to-Stand transition of the patient; determine, based on the at least one accelerometer signal, whether the Sit-to-Stand transition of the patient occurs; determine, based on the Sit-to-Stand transition occurring, a second plurality of pulse transit times after the Sit-to-Stand transition of the patient; and determine a likelihood the patient will fall based on the first plurality of pulse transit times and the second plurality of pulse transit times.

Example 2. The system of example 1, wherein the processing circuitry is configured to determine the likelihood the patient will fall at least in part by calculating a first metric based upon the first plurality of pulse transit times.

Example 3. The system of example 2, wherein the processing circuitry is further configured to determine the likelihood the patient will fall at least in part by calculating second metrics based on the second plurality of pulse transit times and comparing the second metrics to the first metric.

Example 4. The system of example 3, wherein the first metric comprises a median, mean or mode of the first plurality of pulse transit times and the second metrics comprise at least one of a slope of the second plurality of pulse transit times, a minimum pulse transit time of the second plurality of pulse transit times, a maximum pulse transit time of the second plurality of pulse transit times, or a median, mean, or mode of the second plurality of pulse transit times.

Example 5. The system of example 4, wherein the processing circuitry is configured to determine the likelihood the patient will fall at least in part by calculating difference metrics, wherein the difference metrics comprise at least one of a difference between the first metric and a minimum pulse transit time of the second plurality of pulse transit times, a difference between the first metric and a maximum pulse transit time of the second plurality of pulse transit times, or a difference between the first metric and a median, mean or mode of the second plurality of pulse transit times.

Example 6. The system of example 5, wherein the processing circuitry is configured to determine the likelihood the patient will fall at least in part by calculating tendency metrics based on at least one of the difference metrics or the slope of the second plurality of pulse transit times over time.

Example 7. The system of example 6, wherein the processing circuitry is configured to determine the likelihood the patient will fall at least in part by comparing at least one of the difference metrics or the slope of the second plurality of pulse transit times to past tendency metrics.

Example 8. The system of any combination of examples 3-7, wherein the processing circuitry is further configured to determine whether the patient has been inactive for a predetermined period of time prior to calculating the first metric and the second metrics.

Example 9. The system of any combination of examples 1-8, further comprising communication circuitry, the communication circuitry being operable to transmit an alert to an external device upon determining the likelihood the patient will fall has increased.

Example 10. A method comprising: determining, by processing circuitry, a first plurality of pulse transit times prior to a Sit-to-Stand transition of a patient; determining, by processing circuitry and based on at least one accelerometer signal, whether the Sit-to-Stand transition of the patient occurs; determining, by processing circuitry and based on the Sit-to-Stand transition occurring, a second plurality of pulse transit times after the Sit-to-Stand transition of the patient; and determining a likelihood the patient will fall based on the first plurality of pulse transit times and the second plurality of pulse transit times.

Example 11. The method of example 10, wherein the determining the likelihood the patient will fall comprises calculating a first metric based upon the first plurality of pulse transit times.

Example 12. The method of example 11, wherein the determining the likelihood the patient will fall further comprises calculating second metrics based on the second plurality of pulse transit times and comparing the second metrics to the first metric.

Example 13. The method of example 12, wherein the first metric comprises a median, mean or mode of the first plurality of pulse transit times and the second metrics comprise at least one of a slope of the second plurality of pulse transit times, a minimum pulse transit time of the second plurality of pulse transit times, a maximum pulse transit time of the second plurality of pulse transit times, or a median, mean, or mode of the second plurality of pulse transit times.

Example 14. The method of example 13, determining the likelihood the patient will fall further comprises calculating difference metrics, wherein the difference metrics comprise at least one of a difference between the first metric and a minimum pulse transit time of the second plurality of pulse transit times, a difference between the first metric and a maximum pulse transit time of the second plurality of pulse transit times, or a difference between the first metric and a median, mean or mode of the second plurality of pulse transit times.

Example 15. The method of example 14, the determining the likelihood the patient will fall further comprises calculating tendency metrics based upon at least one of the difference metrics or the slope of the second plurality of pulse transit times over time.

Example 16. The method of example 15, the determining the likelihood the patient will fall further comprises comparing at least one of the difference metrics or the slope of the second plurality of pulse transit times to past tendency metrics.

Example 17. The method of any combination of examples 12-16, further comprising determining that the patient has been inactive for a predetermined period of time prior to calculating the first metric and the second metrics.

Example 18. The method of any combination of examples 10-17, further comprising transmitting, by communication circuitry and based on determining the likelihood the patient will fall increased, an alert to an external device.

Example 19. A non-transitory computer-readable storage medium comprising instructions, that when executed by processing circuitry of a device, cause the device to: determine a first plurality of pulse transit times prior to a Sit-to-Stand transition of a patient; determine whether the Sit-to-Stand transition of the patient occurs based on at least one accelerometer signal; determine a second plurality of pulse transit times after the Sit-to-Stand transition of the patient; and determine a likelihood the patient will fall based upon the first plurality of pulse transit times and the second plurality of pulse transit times.

Example 20. The non-transitory computer-readable storage medium of example 19, wherein the instructions cause the device to determine the likelihood the patient will fall by calculating a first metric based upon the first plurality of pulse transit times.

Various aspects of the disclosure have been described. These and other aspects are within the scope of the following claims.

What is claimed is:

1. An insertable cardiac monitoring device configured to be subcutaneously inserted into a patient comprising:
   a housing;
   accelerometer circuitry configured to generate at least one accelerometer signal;
   at least one of a) a plurality of electrodes, at least one of the plurality of electrodes being disposed on a proximal portion of the housing and at least another one of the plurality of electrodes being disposed on a distal portion of the housing, or b) a plurality of light detectors, at least one of the plurality of light detectors being disposed on the proximal portion of the housing and at least another one of the plurality of detectors being disposed on the distal portion of the housing;
   sensing circuitry configured to monitor sensed signals via the at least one of the plurality of electrodes or the plurality of light detectors;
   a memory; and
   processing circuitry communicatively coupled to the accelerometer circuitry, the sensing circuitry, and the memory, the processing circuitry being configured to:
      determine, based on the sensed signals, a first plurality of pulse transit times of the patient prior to a Sit-to-Stand transition of the patient;
      determine, based on the at least one accelerometer signal, whether the Sit-to-Stand transition of the patient occurs;
      determine, based on the sensed signals and in response to the Sit-to-Stand transition occurring, a second plurality of pulse transit times after the Sit-to-Stand transition of the patient;
      calculate a first metric comprising a median, mean or mode of the first plurality of pulse transit times;
      calculate a plurality of second metrics based on the second plurality of pulse transit times, the plurality of second metrics comprising a slope of the second plurality of pulse transit times and at least one of a minimum pulse transit time of the second plurality of pulse transit times, maximum pulse transit time of the second plurality of pulse transit times, or a median, mean, or mode of the second plurality of pulse transit times; and
      determine a likelihood the patient will fall based on the first metric and the plurality of second metrics.

2. The insertable cardiac monitoring device of claim 1, wherein the processing circuitry is configured to determine the likelihood the patient will fall at least in part by calculating difference metrics, wherein the difference metrics comprise at least one difference between the first metric and one or more of the plurality of second metrics.

3. The insertable cardiac monitoring device of claim 2, wherein the processing circuitry is configured to determine the likelihood the patient will fall at least in part by calculating tendency metrics, the tendency metrics comprising at least one of a) a mean, median, or mode of at least one of the difference metrics or the slope of the second plurality of pulse transit times over time and at least one of b) a standard deviation or range of at least one of the difference metrics or the slope of the second plurality of pulse transit times over time.

4. The insertable cardiac monitoring device of claim 3, wherein the processing circuitry is configured to determine the likelihood the patient will fall at least in part by comparing at least one of the difference metrics or the slope of the second plurality of pulse transit times to the tendency metrics.

5. The insertable cardiac monitoring device of claim 1, wherein the processing circuitry is further configured to determine that the patient has been inactive for a predetermined period of time prior to the Sit-to-Stand transition and wherein the processing circuitry is configured to calculate the first metric and calculate the plurality of second metrics based on the determination that the patient has been inactive for the predetermined period of time prior to the Sit-to-Stand transition.

6. The insertable cardiac monitoring device of claim 1, further comprising communication circuitry, the communication circuitry being operable to transmit an alert to an external device upon determining the likelihood the patient will fall has increased.

7. A method for controlling operation of an insertable cardiac monitoring device configured to be subcutaneously inserted into a patient to determine a likelihood that the patient will fall comprising:
   determining, by processing circuitry of the insertable cardiac monitoring device, a first plurality of pulse transit times prior to a Sit-to-Stand transition of the patient based on sensed signals, the sensed signals being sensed via at least one of a) a plurality of electrodes, at least one of the plurality of electrodes being disposed on a proximal portion of a housing of the insertable cardiac monitor and at least another one of the plurality of electrodes being disposed on a distal portion of the housing, or b) a plurality of light detectors, at least one of the plurality of light detectors being disposed on the proximal portion of the housing and at least another one of the plurality of detectors being disposed on the distal portion of the housing;
   determining, by the processing circuitry and based on at least one accelerometer signal from an accelerometer of the insertable cardiac monitoring device, whether the Sit-to-Stand transition of the patient occurs;
   determining, by the processing circuitry and in response to the Sit-to-Stand transition occurring, a second plurality of pulse transit times after the Sit-to-Stand transition of the patient based on the sensed signals;
   calculating, by the processing circuitry, a first metric comprising a median, mean or mode of the first plurality of pulse transit times;
   calculating, by the processing circuitry, a plurality of second metrics based on the second plurality of pulse transit times, the plurality of second metrics comprising a slope of the second plurality of pulse transit times and at least one of a minimum pulse transit time of the second plurality of pulse transit times, a maximum pulse transit time of the second plurality of pulse transit times, or a median, mean, or mode of the second plurality of pulse transit times; and
   determining, by the processing circuitry, the likelihood the patient will fall based on the first metric and the plurality of second metrics.

8. The method of claim 7, wherein the determining the likelihood the patient will fall further comprises calculating difference metrics, wherein the difference metrics comprise at least one difference between the first metric and one or more of the plurality of second metrics.

9. The method of claim 8, wherein the determining the likelihood the patient will fall further comprises calculating tendency metrics, the tendency metrics comprising at least one of a) a mean, median, or mode of at least one of the difference metrics or the slope of the second plurality of pulse transit times over time and at least one of b) a standard deviation or range of at least one of the difference metrics or the slope of the second plurality of pulse transit times over time.

10. The method of claim 9, wherein the determining the likelihood the patient will fall further comprises comparing at least one of the difference metrics or the slope of the second plurality of pulse transit times to the tendency metrics.

11. The method of claim 7, further comprising determining, by the processing circuitry, that the patient has been inactive for a predetermined period of time prior to the Sit-to-Stand transition, and wherein calculating the first metric and calculating the plurality of second metrics is based on the determination that the patient has been inactive for the predetermined period of time prior to the Sit-to-Stand transition.

12. The method of claim 7, further comprising transmitting, by communication circuitry and based on determining the likelihood the patient will fall increased, an alert to an external device.

* * * * *